United States Patent [19]
Allen

[11] Patent Number: 5,795,873
[45] Date of Patent: Aug. 18, 1998

[54] METHOD FOR TREATMENT AND PREVENTION OF DEFICIENCIES OF VITAMINS $B_{12}$, FOLIC ACID AND $B_6$

[75] Inventor: Robert H. Allen, Englewood, Colo.

[73] Assignee: Metabolite Laboratories, Inc., Denver, Colo.

[21] Appl. No.: 693,515

[22] Filed: Aug. 2, 1996

Related U.S. Application Data

[62] Division of Ser. No. 999,499, Dec. 29, 1992, Pat. No. 5,563,126.
[51] Int. Cl.$^6$ .......................... A01N 43/04; A01N 43/58; A01N 43/40
[52] U.S. Cl. .......................... 514/52; 514/249; 514/345; 514/814
[58] Field of Search .......................... 514/52, 249, 345, 514/814

[56] References Cited

PUBLICATIONS

Rosenblatt et al., 1987, Amer. J. Med. Gen. 26:377–383.
Brattström et al., 1990, Atheroscler. 81:51–60.
Stabler et al., 1990, Blood 76:871–881.
Lee, Richard G., et al., "Disorders of Red Blood Cells", *Wintrobe's Clinical Hematology*, 1993, pp. 745–790, vol. 1, Ninth Ed., Lea & Febiger, Philadelphia, PA.
Pechet, Liberto, "Anemias and Other Red Cell Disorders", *Textbook of Primary Care Medicine*, 1996, pp. 722–734, 2nd Ed., Mosby–YearBook, Inc. St. Souis, Missouri.
Ueland, Per Magne et al., "Plasma Homocysteine and Cardiovascular Disease", *Artherosclerotic Cardiovascular Disease, Hemostasis, and Endothelial Function*, 1992, pp. 183–236, Marcel Decker, New York, New York.
Ueland, Per Magne et al., "Review Article: Plasma homocysteine, a risk factor for vascular disease: Plasma levels in health, disease, and drug therapy" *The Clinical Pharmacology Unit, Department of Pharmacology and Toxicology*, 1989, pp. 473–501, University of Bergen, Bergen Norway.
Graham, Ian, FRCPI, et al. "Plasma Homocysteine as Risk Factor for Vascular Disease", *JAMA*, 1997, pp. 1775–1781, vol. 277, No. 22, The Adelaide Hospital Peter STreet, Dublin 8, Ireland.
Brattstrom, L.E. et al., "Folic acid—an innocuous means to reduce plasma homocysteine", *Scand J. Clin Lab Invest*, 1988; pp. 215–221, University Hospital, Lund, Sweden.
Stabler, Sally P. et al. "Elevation of Total Homocysteine in the Serum of Patients with Cobalamin or Folate Deficiency Detected by Capillary Gas Chromatography–Mass Spectrometry", *The American Society for Clinical Investigation, Inc.*, 1988, pp. 466–474, vol. 81, J. Clin. Invest. 0021–9738/88/02/0466/09.
Wilcken, D.E.L., "Homocysteine in the plasma of renal transplant recipients: effects of cofactors for methionine metabolism", *Clinical Science*, 1981, pp. 743–479, vol. 61, Sydney New South Wales, Australia.

Wilcken, David E.L. et al., "Homocystinuria Due to Cystathionine B–Synthase Deficiency—The Effects of Betaine Treatment in Pyridoxine–Responsive Patients", *Metabolism*, 1985, pp. 1115–1121, vol. 34, No. 12, Sydney, N.S.W., Australia.
Brattstrom, Lars E., et al., "Folic Acid Responsive Postmenopausal Homocysteinemia", *Metabolism*, 1985, pp. 1073–1077, vol. 34, No. 11, Lund, Sweden.
Olszewski, Andrzej J. et al., "Reduction of plasma lipid and homocysteine levels by pyridoxine, folate, cobalamin, choline, roboflavin, and troxerutin in atherosclerosis", *Atherosclerosis*, 1989, pp. 1–6, vol. 75, Elsevier Scientific Publishers, Ireland, Ltd. 0021–9150/89.
Arnesen, Egil et al., "Serum Total Homocysteine and Coronary Heart Disease", *International Journal of Epidemiology*, 1995, pp. 704–709, vol. 24, No. 4, Great Brittan.
Mason, Joel B., et al., "The Effects of Vitamins$_a$ $B_{12}$, $B_6$, and Folate on Blood Homocysteine Levels" *Annals of the New York Academy of Sciences*, pp. 197–204, vol. 669, New York, New York.
Franken, Diana G., et al., "Treatment of Mild Hyperhomocysteinemia in Vascular Disease Patients" *Arteriosclerosis and Thrombosis*, pp. 465–470, vol. 14, No. 3, (1994).
Van Den Berg, Michaiel, et al., "Combined vitamin $B_6$ plus folic acid therapy in young patients with arteriosclerosis and hyperhomocysteinemia", *Journal of Vascular Surgery*, 1994, vol. 20, No. 6, pp. 933–940.
"Homocysteine, Folic Acid, and the Prevention of Vascular Disease", *Nutrition Reviews* pp. 247–249, vol. 47, No. 8.

(List continued on next page.)

*Primary Examiner*—Laurie Scheiner
*Assistant Examiner*—Jeffrey S. Parkin
*Attorney, Agent, or Firm*—Davis, Graham & Stubbs LLP

[57] ABSTRACT

A method for orally administering vitamin preparations is described which combine vitamin $B_{12}$ ($B_{12}$, cobalamin) and folic acid (folate), with and without pyridoxine ($B_6$), for preventing and treating elevated serum homocysteine (HC), cystathionine (CT), methylmalonic acid (MMA), or 2-methylcitric acid (2-MCA) levels. These metabolites have been shown to be indicative of $B_{12}$ and/or folic acid deficiencies. Further, it is likely that a $B_6$ deficiency may be present with a $B_{12}$ or folate deficiency. The method of the invention is also for use in lowering serum HC, CT, MMA, or 2-MCA in patients with or at risk for neuropsychiatric, vascular, renal or hematologic diseases. One embodiment of the invention is the use of a non-prescription formulation containing 2.0 mg $B_{12}$ and 0.4 mg folic acid, with and without 25 mg $B_6$. Another embodiment uses a prescription strength formulation containing 2.0 mg $B_{12}$ and 1.0 mg folic acid, with and without 25 mg $B_6$. The method of the present invention eliminate the costly and time consuming steps of distinguishing between vitamin deficiencies once a deficiency is found by measurement of serum metabolite levels. The present invention is of particular benefit to the populations at risk for elevated serum metabolite levels, such as the people over the age of 65, and populations that have or are at risk for neuropsychiatric, vascular, renal and hematologic diseases.

48 Claims, 11 Drawing Sheets

OTHER PUBLICATIONS

Kang, Soo–Sang et al., "Hyperhomocyst(e)inemia as a Risk Factor for Occlusive Vascular Disease", *Annu. Rev. Nutr.* 1992, pp. 279–298, vol. 12:279–98.

Stampfer, Meir J., et al., "A Prospective Study of Plasma Homocyst(e)ine and Risk of Myocardial Infarction in US Physcicians", *JAMA*, 1992, pp. 877–881, vol. 268, No. 7.

Stampfer, Meir J., et al., "Homocysteine and Marginal Vitamin Deficiency The Importance of Adequate Vitamin Intake", *JAMA*, 1993, pp. 2726–2727 vol. 270, No. 22.

Chasan–Taber, Lisa, et al., "A Prospective Study of Folate and Vitamin $B_6$ and Risk of Myocardial Infarction in US Physicians", *Journal of the American College of Nutrition*, pp. 136–143, vol. 15, No. 2.

Harpey, Jean–Paul, "Hemocystinuira caused by 5, 10 methylenetetrahydrofolate reductase deficiency: A case in an infant responding to methionine, folinic acid, pyridoxine, and vitamin $B_{12}$ therapy", *The Journal of Pediatrics*,1981, pp. 275–278, vol. 98 No. 2 (The C.V. Mosby Co.).

Wilcken, David, "Folic Acid Lowers Elevated Plasma Homocysteine in Chronic Renal Insufficiency: Possible Implications for Prevention of Vascular Disease", *Metabolism*, 1988, pp. 697–701, vol. 37, No. 7 (Jul.) Sydney N.S.W., Australia.

METHOD FOR TREATMENT AND PREVENTION OF DEFICIENCIES OF VITAMINS $B_{12}$, FOLIC ACID AND $B_6$

This application is a divisional of application Ser. No. 07/999,499 filed Dec. 29, 1992, now U.S. Pat. No. 5,563,126.

FIELD OF THE INVENTION

This invention relates to the field of nutrition. Specifically, the invention is comprised of new oral vitamin preparations combining vitamin $B_{12}$ ($B_{12}$, cobalamin) and folic acid (folate), and vitamin $B_{12}$, folate, and pyridoxine ($B_6$) for use in patients with elevated serum metabolite levels of homocysteine (HC), cystathionine (CT), methylmalonic acid (MMA), or 2-methylcitric acid (2-MCA). The elevation of these metabolites has been shown to be indicative of tissue deficiencies of $B_{12}$ and/or folate and/or $B_6$, and related to increased risk of neuropsychiatric, vascular, renal and hematologic diseases. One embodiment of the present invention uses a non-prescription formulation comprising between 0.3–10.0 mg $B_{12}$ and 0.1–0.4 mg folate, with the preferred embodiment using 2.0 mg $B_{12}$ and 0.4 mg folate. Another embodiment of the non-prescription formulation uses 0.3–10 mg $B_{12}$, 0.1–0.4 mg folate, and 5–75 mg $B_6$, with the preferred embodiment using 2.0 mg $B_{12}$, 0.4 mg folate, and 25 mg $B_6$. Another embodiment of the present invention uses a prescription strength formulation comprising between 0.3–10.0 mg $B_{12}$ and 0.4–1.0 mg folate, with the preferred embodiment using 2 mg $B_{12}$ and 1.0 mg folate. In a further embodiment of the present invention, a prescription strength formulation is used comprising 0.3–10 mg $B_{12}$, 0.4–1.0 mg folate, and 5–75 mg $B_6$, with the preferred embodiment using 2 mg $B_{12}$, 1.0 mg folate, and 25 mg $B_6$. The formulations of the present invention eliminate the costly and time-consuming steps of distinguishing between vitamin deficiencies once a deficiency is found by measurement of serum metabolite levels. The present invention is of particular benefit to the populations at risk for tissue deficiencies of $B_{12}$, folate, and $B_6$, such as people over the age of 65, and populations that have or are at risk for neuropsychiatric, vascular, renal and hematologic diseases.

BACKGROUND

Vitamins $B_{12}$, folate, and $B_6$ are required cofactors in metabolic pathways involving methionine, homocysteine, cystathionine, and cysteine. $B_{12}$ in the form of 5'-deoxyadenosylcobalamin is an essential cofactor in the enzymatic conversion of methylmalonylCoA to succinyl-CoA. The remethylation of homocysteine (HC) to methionine catalyzed by methionine synthase requires folate (methyltetrahydrofolate) and $B_{12}$ in the form of methylcobalamin. HC is condensed with serine to form cystathionine (CT) in a reaction catalyzed by cystathionine β-synthase which requires $B_6$ (pyridoxal phosphate). CT is hydrolyzed in another $B_6$-dependent reaction to cysteine and α-ketobutyrate.

It is important to diagnose and treat $B_{12}$, folate, and $B_6$ deficiencies because these deficiencies can lead to life-threatening hematologic abnormalities which are completely reversible by proper treatment. $B_{12}$ deficiency is a multisystem disorder with extremely varied clinical presentation which has been thought to occur in 0.4% of the population, e.g., about 1 million people in the United States. Symptoms of $B_{12}$ deficiency include significant anemia, displayed for example in decreased hematocrit (e.g., <25%) or hemoglobin (e.g., ≦8 g %), with macrocytic red blood cells (i.e., mean cell volume generally greater than 100 fl), or neurologic symptoms of peripheral neuropathy and/or ataxia. See, for example, Babior and Bunn (1983) in Harrison's Principles of Internal Medicine, (Petersdorf et al., eds.), McGraw-Hill Book Co., New York; Lee and Gardner (1984) in Textbook of Family Practice, 3rd Ed. (Rakel, ed.), Saunders & Co., Philadelphia). The hematological abnormalities seen are due to intracellular folate deficiency since folate is required for a number of essential enzymatic reactions involved in DNA and RNA synthesis and since the form of folate in serum (5-methyltetrahydrofolate) must be metabolized to tetrahydrofolate by the $B_{12}$-dependent enzyme methionine synthase before it can be utilized by the RNA- and DNA-related enzymes. While it has been well recognized that individuals with $B_{12}$ deficiency could display neurologic disorders in the absence of anemia, such situations were believed to be exceptional and rare. See, Beck (1985) in Cecil Textbook of Medicine, 17th Ed., (Wyngaarden and Smith, eds.), W. B. Saunders, Philadelphia, pp. 893–900; Babior and Bunn (1987) in Harrison's Principles of Internal Medicine, 11th Ed., (Braunwald et al., eds.) McGraw-Hill, New York, pp. 1498–1504; Walton (1985) in Brain's Diseases of the Nervous System, 9th Ed., Oxford University Press, Oxford, UK. The neurologic symptoms of $B_{12}$ deficiency were considered to be late manifestations of the disease most typically occurring after the onset of anemia or, if they occurred first, were soon to be followed by the onset of anemia. See, Woltmann (1919) Am. J. Med. Sci. 157:400–409; Victor and Lear (1956) Am. J. Med. 20:896–911.

However, it has recently been shown that the textbook description of severe megaloblastic anemia and combined systems disease of the nervous system is the rarest presentation of $B_{12}$ deficiency at the present time (Stabler et al. (1990) Blood 76:871–881; Carmel (1988) Arch. Int. Med. 148:1712–1714; Allen (1991) in Cecil Textbook of Medicine, 19th Ed., (Wyngaarden and Smith, et al. eds.), W. B. Saunders, Philadelphia, pp. 846–854.). Therefore, contrary to previous teachings, patients that may benefit from $B_{12}$ therapy may have minimal to no hematologic changes while manifesting a wide variety of neurologic and psychiatric abnormalities (Lindenbaum et al. (1988) N. Engl. J. Med. 318:1720–1728; Greenfield and O'Flynn (1933) Lancet 2:62–63). This is particularly true for populations at risk for $B_{12}$ deficiency, such as the elderly population (Pennypacker et al. (1992) J. Am. Geriatric Soc. 40: (in press).

The incidence of folate deficiency in the population is unknown, but has been thought to occur commonly in individuals with various degrees of alcoholism. The hematologic abnormalities seen with folate deficiency, such as macrocytic anemia, are indistinguishable from those seen with $B_{12}$ deficiency. Folate is required for a number of essential enzymatic reactions involved in DNA and RNA synthesis, and is particularly important in rapidly dividing cells like those in the bone marrow.

$B_6$ is required for the first step in heme synthesis and serves a major role in transamination reactions of amino acid metabolism, in decarboxylations, and in the synthesis of the neuroactive amines histamine, tyramine, serotonin, and γ-aminobutyric acid (GABA). Clinical manifestations include microcytic hypochromic anemia, characteristic skin changes of dermatitis and acrodynia, muscular weakness, and a variety of neuropsychiatric abnormalities including hyperirritability, epileptiform confusions, depression and confusion (Newberne and Conner (1989) in Clinical Biochemistry of Domestic Animals, Academic Press, San Diego, pp. 796–834).

Vitamin deficiencies are generally determined by measurement of serum levels. Normal serum $B_{12}$ levels are 200–900 pg/ml, with levels of less than 100 pg/ml being said to indicate clinically significant deficiency (Beck (1985) supra) However, serum $B_{12}$ levels are a relatively insensitive determinant of $B_{12}$ deficiency in that only 50% of patients with clinically confirmed $B_{12}$ deficiency have levels less than 100 pg/ml, 40% are 100–200 pg/ml, and at least 5–10% have values in the 200–300 pg/ml range. Diagnosis is further complicated by the fact that 2.5% of normal subjects (6,250,000 people in the U.S.) have low serum $B_{12}$ levels (Allen (1991) supra), with no evidence of $B_{12}$ deficiency and are unlikely to benefit from $B_{12}$ therapy (Schilling et al. (1983) Clin. Chem. 29:582; Stabler (1990) supra).

Normal serum folate levels are 2.5–20 ng/ml, with levels less than 2.5 ng/ml indicating the possibility of clinically significant deficiency. Like $B_{12}$ serum levels, however, serum folate levels are a relatively insensitive measure in that only 50–75% of patients with folate deficiency have levels less than 2.5% ng/ml, with most of the remaining 25–50% being in the 2.5–5.0 ng/ml range (Allen (1991) in Cecil Textbook of Medicine, 19th Ed., supra).

The development of sensitive serum metabolite assays for HC, CT, MMA, and 2-MCA has allowed the relationship between metabolite levels and vitamin deficiencies to be investigated (Stabler et al. (1987) Anal. Biochem. 162:185–196; Stabler et al. (1986) J. Clin. Invest. 77:1606–1612; Stabler et al. (1988) J. Clin. Invest. 81:466–474). It has been found that elevated serum levels of HC and MMA are clinically useful tests of functional intracellular deficiencies of $B_{12}$ and folate, with elevated HC levels seen with both $B_{12}$ and folate deficiencies, and elevated MMA levels seen with a $B_{12}$ deficiency (Allen et al. (1990) Am. J. Hematol. 34:90–98; Lindenbaum et al. (1990) Am. J. Hematol. 34:99–107; Lindenbaum et al. (1988) N. Engl. J. Med. 318:1720–1728; Beck (1991) in Neuropsychiatric Consequences of Cobalamin Deficiency, Mosby Year Book 36:33–56; Moelby et al. (1990) 228:373–378; Ueland and Refsum (1989() J. Lab. Clin. Med. 114:473–501; Pennypacker et al. (1992) supra). Increased serum levels of CT are seen in both deficiencies and 2-MCA is elevated in $B_{12}$ deficiency (Allen et al. (1991) in Proceedings of the 1st International Congress on Vitamins and Biofactors in Life Science, Kobe (Japan); Allen et al. (1993) Metabolism (in press)). HC and CT may be elevated in patients with intracellular deficiency of $B_6$, but this has not been as well documented (Park and Linkswiler (1970) J. Nutr. 100:110–116; Smolin and Benvange (1982) J. Nutr. 112:1264–1272).

Elevated serum metabolite levels are observed in disease states other than classic vitamin deficiencies. For example, elevated HC levels have been observed in the presence of vascular disease. The homocysteine theory of -atherosclerosis, formulated by McCully and Wilson (1975) Atherosclerosis 22:215–227, suggests that high levels of HC are responsible for the vascular lesions seen in homocystinuria, a genetic defect caused by a deficiency in the enzyme cystathionine β-synthase. The theory also implies that moderate elevations of HC might be associated with increased risk for vascular disease (Ueland et al. (1992) in Atherosclerotic Cardiovascular Disease, Hemostasis, and Endothelial Function (Francis, Jr., ed.), Marcel Dekker, Inc., New York, pp. 183–236). Moderate hyperhomocysteinaemia has been shown to be frequently present in cases of stroke and to be independent of other stroke risk factors (Brattstrom et al. (1992) Eur. J. Clin. Invest. 22:214–221). Clinical and experimental evidence demonstrates that patients who are homozygotes for cystathionine β-synthase deficiency have a markedly increased incidence of vascular disease and thrombosis. A number of studies (see, Clarke et al. (1991) N. Engl. J. Med. 324:1149–1155) strongly suggest that heterozygotes for a deficiency of cystathionine β-synthase also have an increased incidence of vascular disease and thrombosis and that such heterozygotes may constitute as many as one-third of all patients who develop strokes, heart attacks, or peripheral vascular disease under age 50. It is also likely that such heterozygotes are also at increased risk for vascular disease and thrombosis after age 50. Since the incidence of heterozygosity for cystathionine β-synthase deficiency is estimated to be 1 in 60–70, this means that there are approximately 4 million heterozygotes in the U.S. It is also possible that patients with vascular disease due to other causes, such as hypercholesterolemia, would also benefit from a decrease in their serum HC levels even if their existing levels are only slightly elevated or actually within the normal range.

Renal disease is another condition that gives rise to elevated levels of serum metabolites. Approximately 75% of patients with renal disease have elevated serum concentrations of HC, CT, MMA, and 2-MCA. Since patients with renal disease have a significant incidence and marked acceleration of vascular disease, it might be beneficial to lower their serum metabolite levels, especially that of HC.

An increasing prevalence of low serum $B_{12}$ concentrations with advancing age has been found by many but not all investigators (Bailey et al. (1980) J. Am. Geriatr. Soc. 28:276–278; Eisborg et al. (1976) Acta Med. Scand. 200:309–314; Niisson-Ehle et al. (1989) Dig. Dis. Sci. 34:716–723; Norman (1985) 33:374; Hitzhusen et al. (1986) Am. J. Clin. Pathol. 85:3236), folate (Magnus et al. (1982) Scan. J. Haematol. 28:360–366; Blundell et al. (1985) J. Clin. Pathol. 38:1179–1184; Elwood et al. (1971) Br. J. Haematol. 21:557–563; Garry et al. (1984) J. Am. Geriatr. Soc. 32:71926; Hanger et al. (1991) J. Am. Geriatr. Soc. 39:1155–1159), and $B_6$ (Ranke et al. (1960) J. Gerontol. 15:41–44; Rose et al. (1976) Am. J. Clin. Nutr. 29:847–853; Baker et al. (1979) J. Am. Geriatr. Soc. 27:444–450). Moreover, prevalence estimates for these vitamin deficiencies vary widely depending on the population groups studied. It has been unclear whether this increased prevalence is a normal age related phenomena or a true reflection of tissue vitamin deficiency and whether the low serum vitamin concentrations are a reliable indicator of functional intracellular deficiency.

It is difficult, expensive and time-consuming to distinguish between deficiencies of vitamins $B_{12}$, folate, and $B_6$. The hematologic abnormalities seen with $B_{12}$ deficiency are indistinguishable from those seen with folate deficiency. Similarly to a $B_{12}$ deficiency, $B_6$ deficiencies also result in hematologic as well as neuropsychiatric abnormalities. The traditional methods of determining deficiencies by measurement of serum vitamin levels are often insensitive. As a result, in order to determine if and which vitamin deficiency is present, a patient will be treated with one vitamin at a time and the response to that vitamin determined by normalization of serum vitamin levels and the correction of hematologic abnormalities. These steps are then repeated with each vitamin. This method of treatment is both expensive and time-consuming. In the presence of multiple deficiencies, the diagnosis of vitamin deficiencies is further confused and give rise to the dangerous possibility that only one deficiency will be treated. For example, the hematologic abnormalities seen with a $B_{12}$ deficiency will respond to treatment with folate alone. However, the neuropsychiatric abnormalities caused by the $B_{12}$ deficiency will not be corrected and may indeed by worsened.

It has now been discovered for the first time that the prevalence of intracellular deficiencies of vitamins $B_{12}$, folate, and $B_6$, alone or in combination, is substantially higher than that previously estimated by measurement of serum vitamin concentrations. The present disclosure establishes that tissue deficiencies of one or more of the vitamins $B_{12}$, folate and $B_6$, as demonstrated by the elevated metabolite concentrations, occurs commonly in the elderly population even when serum vitamin levels are normal. Based on this new discovery, the present invention addresses the problem of distinguishing between vitamin deficiencies when low, low-normal, or normal serum vitamin concentrations are found by providing formulations for the treatment of high serum metabolites and at-risk populations for combinations of one or more tissue deficiencies of vitamins $B_{12}$, folate, and $B_6$.

Hathcock and Troendle (1991) JAMA 265:96–97, have suggested the treatment of pernicious anemia with an oral pill containing 300 to 1000 ug or more per day of $B_{12}$. However, contrary to the present invention, Hathcock and Troendle teach away from combining $B_{12}$ therapy with folate, since "if the oral cobalamin therapy should fail to maintain adequate levels, folate might provide protection against development of anemia while permitting nerve damage from cobalamin deficiency."

U.S. Pat. No. 4,945,083, issued Jul. 31, 1990 to Jansen, entitled: Safe Oral Folic-Acid-Containing Vitamin Preparation, describes a oral vitamin preparation comprising 0.1–1.0 mg $B_{12}$ and 0.1–1.0 mg folate for the treatment or prevention of megaloblastic anemia. This formulation presents a problem in the case of a $B_{12}$ deficient patient, in that the 0.5 mg folate may correct the hematologic abnormalities present, but the 0.5 mg $B_{12}$ dose may be insufficient to correct a $B_{12}$ deficiency due to inadequate intrinsic factor. By contrast, the formulation of the present invention teaches the use of the combination of $B_{12}$ and folate, and of $B_{12}$, folate and $B_6$, sufficient to treat either single or multiple deficiencies of $B_{12}$ folate, and $B_6$. The present invention does not rely on the determination of vitamin deficiencies by the measurement of serum vitamin levels, but uses the more sensitive measurement of elevated serum metabolites of HC, CT, MMA, and 2-MCA, shown to be related to the presence of $B_{12}$ and/or folate and/or to $B_6$ deficiencies or to the presence of the increased risk of neuropsychiatric, vascular, renal, and hematologic diseases.

It is to be understood that both the foregoing general description and the following detailed description are exemplary and explanatory only and are not restrictive of the invention as claimed.

SUMMARY OF THE INVENTION

This invention includes a method for orally administering two new vitamin preparations containing vitamin $B_{12}$ and folate, and vitamin $B_{12}$, folate and $B_6$, for the treatment of patients with elevated serum metabolites, such as homocysteine, cystathionine, methylmalonic acid, and 2-methylcitric acid, as well as populations at risk for tissue deficiencies in one or more of the vitamins $B_{12}$, folate, and $B_6$ or for neuropsychiatric, vascular, renal, or hematologic diseases.

One embodiment of the present invention is uses an over-the-counter formulation comprised of between 0.3–10 mg CN-cobalamin ($B_{12}$) and 0.1–0.4 mg folate. Another embodiment of the non-prescription formulation uses 0.3–10 mg $B_{12}$, 0.1–0.4 folate, and 5–75 mg $B_6$. Preferred embodiments of the over-the-counter formulation are comprised of about 2.0 mg $B_{12}$ and 0.4 mg folate, and 2.0 mg $B_{12}$, 0.4 mg folate, and 25 mg $B_6$, respectively.

Another embodiment of the present invention uses a prescription formulation comprised of between 0.3–10 mg CN-cobalamin ($B_{12}$) and 0.4–10.0 mg folate. Another embodiment of the prescription formulation of the present invention uses 0.3–10 mg $B_{12}$, 0.4–1.0 mg folate, and 5–75 mg $B_6$. Preferred embodiments of the prescription formulation use about 2.0 mg $B_{12}$ and 1.0 mg folate, and 2.0 mg $B_{12}$, 1.0 mg folate, and 25 mg $B_6$, respectively.

DETAILED DESCRIPTION OF THE INVENTION

Figure 1:
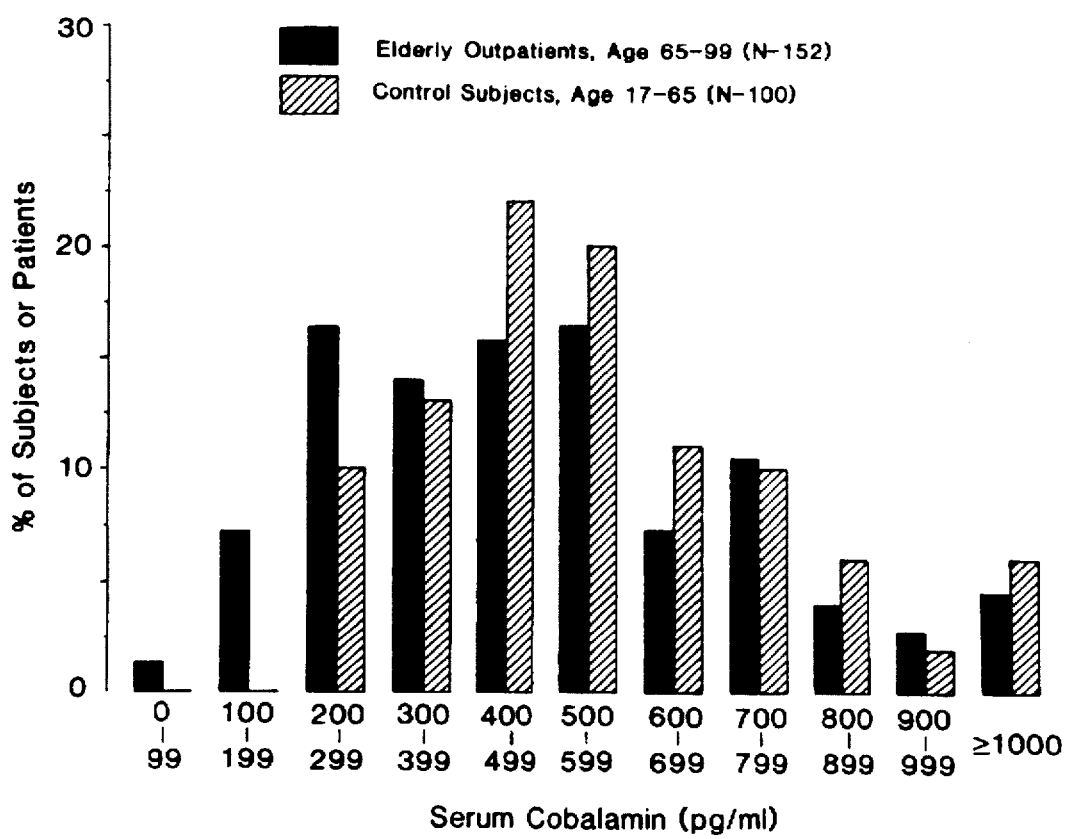
FIG. 1 shows the distribution of serum $B_{12}$ levels for a population of elderly outpatients (ages 65–99, n=152) and a normal population (ages 17–65, n=100).

Reference will now be made in detail to the presently preferred embodiments of the invention, which, together with the following examples, serve to explain the principles of the invention.

This invention uses new oral vitamin formulations combining vitamin $B_{12}$ ($B_{12}$, cobalamin) and folic acid (folate), and vitamin $B_{12}$ folate and pyridoxine ($B_6$) The formulations of the present invention are for use in the treatment of elevated serum levels of one or more the metabolites homocysteine (HC), cystathionine (CT), methylmalonic acid (MMA), or 2-methylcitric acid (2-MCA). The use of the formulations of the present invention further include as a method of lowering serum metabolites levels of one or more of HC, CT, MMA, or 2-MCA, where these metabolite levels are not elevated but the patients are at risk for or have neuropsychiatric, vascular, renal, or hematologic diseases.

One embodiment of the present invention uses a non-prescription formulation comprised of between about 0.3–10 mg CN-cobalamin ($B_{12}$) and 0.1–0.4 mg folate. Another embodiment of the present invention uses a non-prescription formulation comprised of between about 0.3–10 mg $B_{12}$, 0.1–0.4 mg folate, and 5–75 mg $B_6$. Preferred embodiments of the non-prescription formulation are comprised of about 2.0 mg $B_{12}$ and 0.4 mg folate, and 2.0 mg $B_{12}$, 0.4 mg folate, and 25 mg $B_6$, respectively.

Another embodiment of the present invention is comprised of a prescription formulation comprised of between about 0.3–10 mg $B_{12}$ and 0.4–10.0 mg folate, with the preferred embodiment comprised of about 2.0 mg $B_{12}$ and 1.0 mg folate. Another embodiment of the prescription strength formulation is comprised of about 0.3–10 mg $B_{12}$, 0.4–10.0 mg folate, and 5–75 mg $B_6$, with a preferred embodiment comprised of about 2.0 mg $B_{12}$, 1.0 mg folate, and 25 mg $B_6$.

The formulations of the present invention are for the treatment and prevention of elevated metabolite levels in at risk populations, such as the elderly, and people that have or are at risk for neuropsychiatric, vascular, renal and hematologic diseases. The present invention eliminates the costly and time consuming need to differentiate between $B_{12}$, folate, and $B_6$ deficiencies.

The administration of a daily dose of the vitamin formulations of the present invention provides better long-term normalization of serum HC and other metabolites than prior art formulations, and eliminates the difficulty in differentiating between deficiencies of two or three of the vitamins, the difficulty in diagnosing multiple deficiencies of two or three of the vitamins, and the expense of doing so. Further, the administration of an oral preparation of $B_{12}$ and folate, with or without $B_6$, is preferred over intramuscular injections for patient convenience and ease of administration.

For example, the inclusion of $B_{12}$ will be useful as a safeguard for patients misdiagnosed as folate deficient, even though they are actually $B_{12}$ deficient, since treatment with folate alone in such patients is extremely dangerous. The danger arises from the fact that treating a $B_{12}$ deficient patient with folate alone may reverse or prevent the hematologic abnormalities seen in $B_{12}$ deficiency, but will not correct the neuropsychiatric abnormalities of a $B_{12}$ deficiency and may actually precipitate them. Even in the absence of intrinsic factor, approximately 1% of a 2.0 mg oral dose of $B_{12}$ is absorbed by diffusion. Thus, approximately 20 ug of $B_{12}$ would be absorbed from the formulations of the present invention which would be more than adequate even in patients with pernicious anemia who have lost their intrinsic factor-facilitated absorption mechanism for $B_{12}$. The inclusion of folate will be of benefit since $B_{12}$ deficiency causes a secondary intracellular deficiency of folate. The inclusion of folate and $B_6$ will also be of benefit in patients with mixed vitamin deficiencies.

The formulations of the present invention may be administered as a non-injectable implant or orally. Non-injectable use may be as a patch. Formulations for oral administration are preferably encapsulated. Preferably, the capsule is designed so that the formulation is released gastrically where bioavailability is maximized. Additional excipients may be included to facilitate absorption of the vitamin formulations. Diluents, flavorings, low melting point waxes, vegetable oils, lubricants, suspending agents, tablet disintegrating agents, and binders may also be employed.

Example 1 describes the methods used to measure serum vitamin and metabolite levels. Example 2 describes a new study conducted with 412 subjects over the age of 65 with a variety of medical conditions correlating the incidence of low serum vitamin levels with elevated serum metabolite levels. A study determining the incidence of undetected $B_{12}$ deficiency and response of serum MMA and HC to $B_{12}$ treatment in a geriatric outpatient population is described in Example 3. Example 4 describes a similar study conducted with a geriatric nursing home population, and Example 5 describes a similar study conducted with another geriatric population.

EXAMPLE 1.

Methods for Measurement of Serum Vitamin and Metabolite Levels.

Serum vitamin assays. Serum vitamins $B_{12}$ and folate were measured by a quantitative radioassay method using purified intrinsic factor and purified folate binding protein. Vitamin $B_6$ was measured by a radioenzymatic assay method wherein serum is incubated with apoenzyme tyrosine-decarboxylase, $C_{14}$ labelled tyrosine is added to start the enzymatic reaction which is stopped with HCl. Subsequently the free $C_{14}$-labelled $CO_2$ is adsorbed by a KOH impregnated filtering paper. The measured $C_{14}$ activity is directly proportional to the $B_6$ (pyridoxal phosphate) concentration (Laboratory Bioscientia, Germany).

Serum metabolite assays. Serum metabolite assays for homocysteine and methylmalonic acid were conducted by the capillary gas chromatography and mass spectrometry methods of Marcell et al. (1985) Anal. Biochem. 150:58; Stabler et al. (1987) supra, and Allen et al. (1990) Am. J. Hematol. 34:90–98. Serum cystathionine levels were assayed by the method of Stabler et al. (1992) Blood (submitted). Serum 2-methylcitric acid was assayed by the method of Allen et al. (1993) Metabolism supra.

Statistical methods. Statistical analysis was done with the SAS statistical package (version 6.06). Nonparametric data for two or more groups were tested with the two sample Wilcoxon rank sum test (with Bonferroni's correction for the significance level $\alpha$) and the Kruskall Wallis test. From the result of the healthy young subjects reference intervals were calculated. Since the frequency distribution of the values of each parameter were markedly abnormal they were transformed to normal distributions using log transformation. The sample prevalence p with 95% confidence intervals of low serum vitamins $B_{12}$, folate, and $B_6$ concentrations was calculated as (p±2 p (1−p)/n×100 wherein n is the total sample size, p is the number of low serum vitamin concentrations/n; low serum concentrations are defined as <mean—2 S.D.

EXAMPLE 2.

Incidence of Elevated MMA, 2-MCA, HC, and CT Levels in the Geriatric Population.

The serum concentrations of $B_{12}$, folate, and $B_6$ were measured in 412 subjects over the age of 65 (subgroups A–D), and in 99 healthy control subjects aged 20–55 years (subgroup E). The geriatric subgroups were defined as follows: A, 110 patients with atherosclerosis; B, 98 patients with neuropsychiatric disorders; C, 102 patients with atherosclerosis and multiple diseases including rheumatoid arthritis and diabetes; D, 102 subjects who were healthy.

Venous blood was obtained from all subjects in the morning after an overnight fast. The blood was spun within one hour after collection and the serum was transported in dry ice to the central laboratory. Serum vitamins $B_{12}$ and folate were measured as described in Example 1 with a vitamin $B_{12}$/folate dual RIA kit (CT301/CT302 Amersham Buchier, UK). Vitamin $B_6$ and serum metabolites were measured as described in Example 1.

Since renal function can influence serum metabolite concentrations (Ueland and Refsum (1989) supra; Moelby et al. (1992) Scand. J. Clin. Lab. Invest. 52:351–354), serum creatinine concentrations were measured in all subjects by the Jaffe photometric method (Laboratory Bioscientia, Germany). Normal range was 62–124 μmol/L. Creatine clearance was calculated using the formulation of Cockroft and Gault (1976) Nephron 16:31–41.

Normal ranges for serum vitamin and metabolite levels were determined by the mean +2 standard deviations after log normalization using the values from subgroup E. Results are shown in Table 1:

TABLE 1

INCIDENCE OF LOW SERUM VITAMIN AND HIGH METABOLITE LEVELS IN GERIATRIC POPULATIONS A-D AND A YOUNGER HEALTHY POPULATION E.

| Group | $B_{12}$ | Folic Acid | $B_6$ | MMA | 2-MCA | HC | CT |
|---|---|---|---|---|---|---|---|
| A | 6% | 12% | 48% | 36% | 44% | 55% | 64% |
| B | 6% | 19% | 53% | 47% | 39% | 59% | 66% |
| C | 3% | 10% | 50% | 32% | 45% | 39% | 73% |
| D | 6% | 6% | 17% | 26% | 23% | 38% | 41% |
| E | 2% | 1% | 1% | 3% | 6% | 2% | 4% |

There was a rough correlation with low vitamin levels and elevated metabolites, but many of the patients with elevated metabolites had low normal or normal vitamin levels. Correlations between clinical abnormalities within groups A, B, and C were not present. Patients were treated with weekly injections of a multi-vitamin preparation containing 1.0 mg $B_{12}$, 1.1 mg folate, and 5 mg $B_6$, resulting in a marked lowering or normalization of elevated metabolite levels in virtually every elderly patient.

These data support the conclusions that there is an increased incidence of low levels of serum $B_{12}$, folate, and $B_6$ in the geriatric population, and that serum MMA, 2-MCA, HC and CT are elevated in an even higher percentage of geriatric patients. The presence of elevated levels of one or more of the metabolites HC, CT, MMA, or 2-MCA indicate a tissue or intracellular deficiency of one or more of the vitamins $B_{12}$, folate and $B_6$. It not possible to tell without expensive, time-consuming, and extensive testing which one vitamin or pair of vitamins, or whether all three vitamins are deficient. These observations, together with the fact that elevated metabolite levels are corrected by parenteral therapy with a combination of vitamins $B_{12}$, folate, and $B_6$, indicate that a tissue deficiency of one or more of these vitamins occurs commonly in the geriatric population and that measurement of serum vitamin levels alone is an inadequate method for identifying such deficiencies.

EXAMPLE 3.

Determination of Serum $B_{12}$, Folate, MMA, HC, CT and 2-MCA Levels in a Geriatric Outpatient Population.

A study was conducted with 152 elderly outpatient subjects to measure the prevalence of $B_{12}$ deficiency in geriatric outpatients as determined by both low serum $B_{12}$ levels and elevations of MMA and HC, and to determine the response to $B_{12}$ treatment. Blood samples were obtained on 152 consecutive geriatric outpatients, ages 65–99. Control values were determined from 100 subjects, ages 17–65. Serum $B_{12}$, folate, MMA, HC, CT, and 2-MCA levels were obtained for each patient, shown in Table 2. The significance of the results marked as "**" in Table 2 are as follows: $B_{12}$ levels of <200 pg/ml; folate <3.8 ng/ml; homocysteine >16.2 uM; MMA >271 nM; CT >342 nM; and 2-MCA >228 nM. Serum MMA, HC, CT, and 2-MCA levels were measured as described in Example 1. Serum $B_{12}$ and folate were measured as described in Example 1 using a Corning Immophase kit (CIBA-Corning, Medfield, Mass.) with the normal range defined as 200–800 pg/ml for $B_{12}$ and 3.8 ng/ml for folate. After evaluation, patients received weekly parenteral cyanocobalamin injections (1,000 ug IM) for 8 weeks, followed by monthly injections. Repeat laboratory and clinical assessments were administered at 8 weeks and at 6 months.

Figure 2:
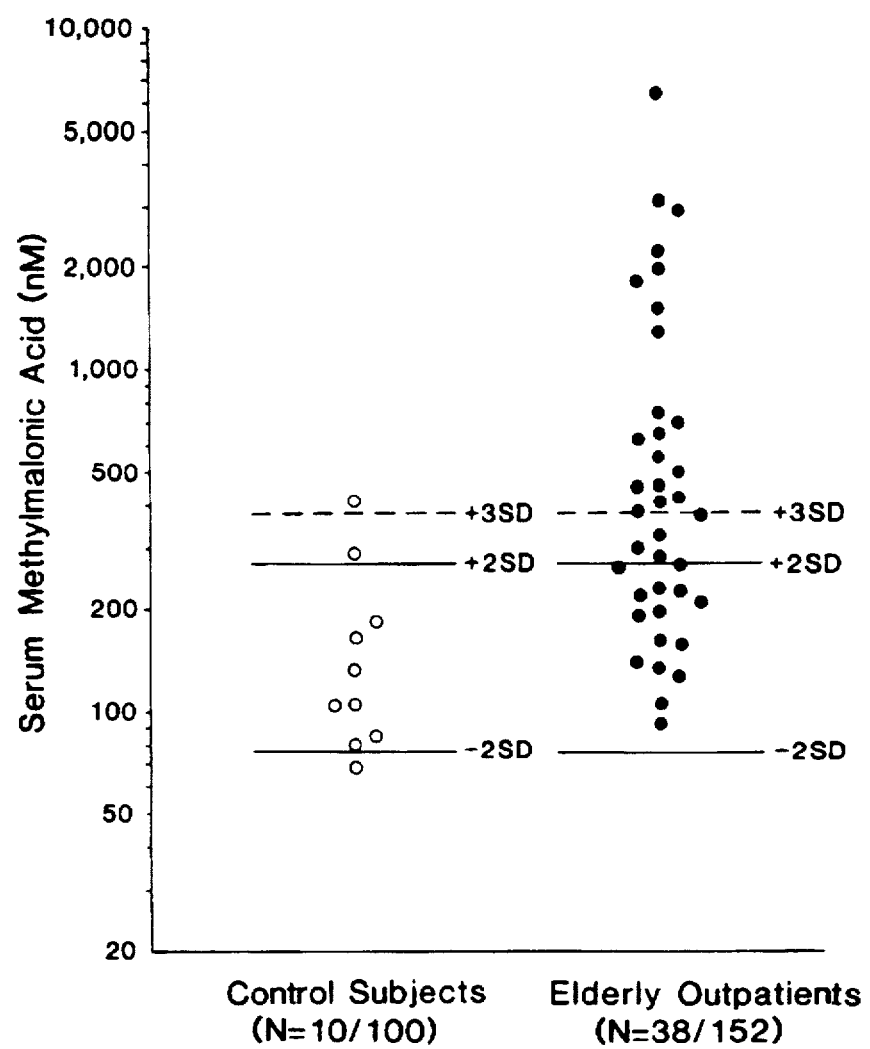
FIG. 2 shows serum MMA levels for a population of elderly outpatients with serum $B_{12}$ values <300 pg/ml (ages 65–99, n=38/152) and a normal population with serum $B_{12}$ values <300 pg/ml (ages 17–65, n=10/100).
Figure 3:
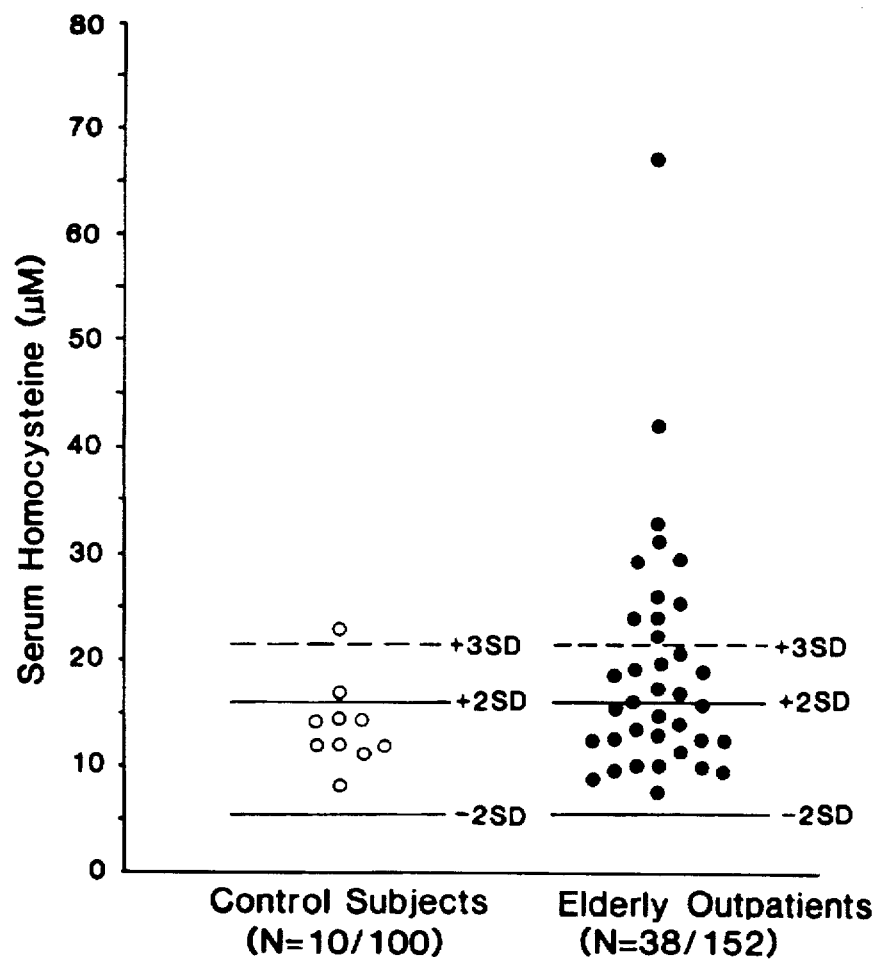
FIG. 3 shows serum HC levels for a population of elderly outpatients with serum $B_{12}$ values <300 pg/ml (ages 65–99, n=38/152) and a normal population with serum $B_{12}$ values <300 pg/ml (ages 17–65, n=10/100).

Results show that 25% of the subjects had a serum $B_{12}$ level ≦300 pg/ml and 8.5% had a low level of <200 pg/ml. FIG. 1 shows the shift seen in elderly subject towards lower serum $B_{12}$ levels. More than half of the subjects with low or low-normal serum $B_{12}$ levels had elevations of MMA (FIG. 2) and/or HC (FIG. 3) greater than 3 S.D. above the means in normals and representing 14.5% of the total screened population.

Figure 4:
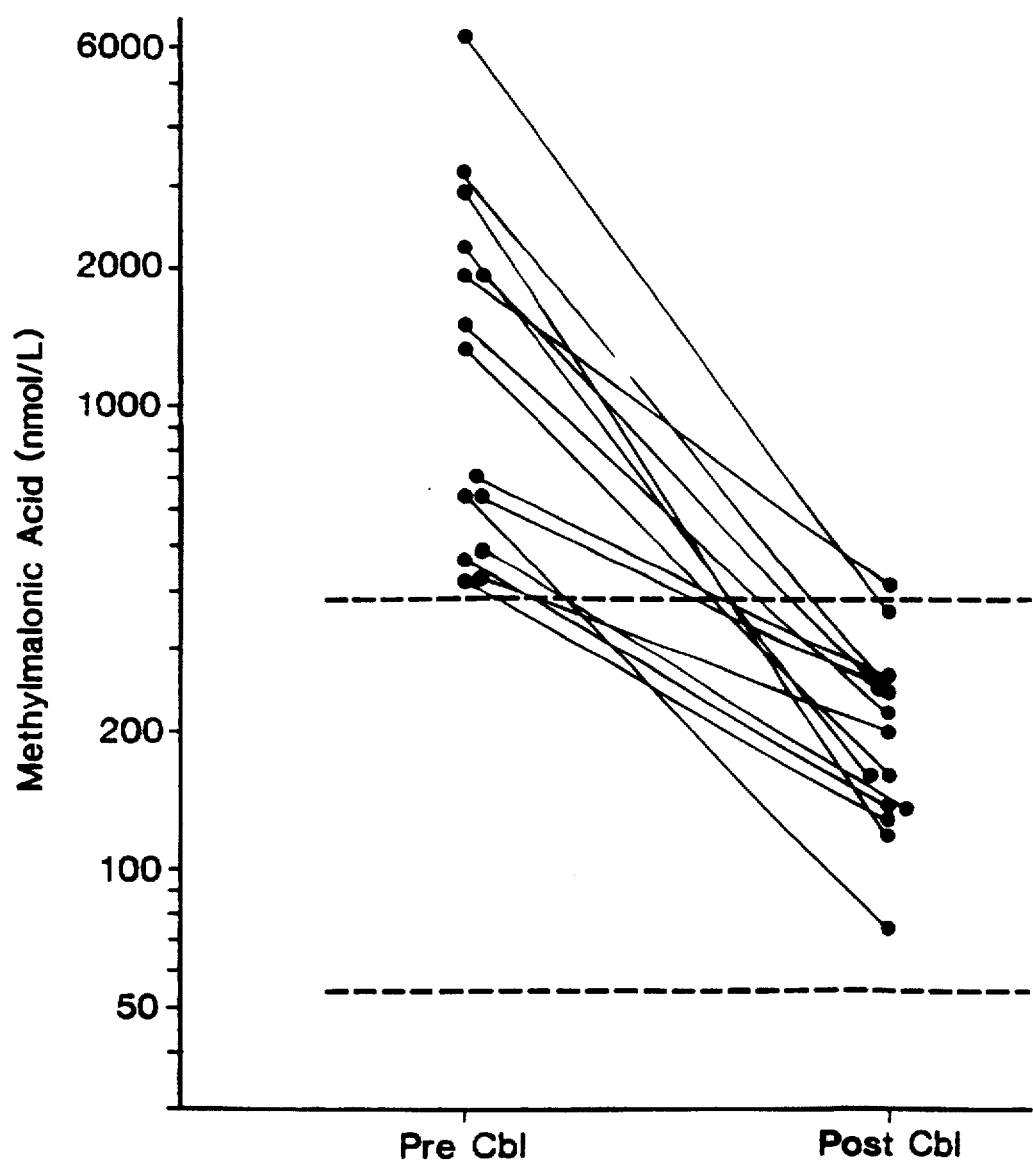
FIG. 4 shows serum MMA levels before and after treatment with parenteral cobalamin for a population of elderly outpatients with elevated MMA values and serum $B_{12}$ values <300 pg/ml (ages 65–99, n=15/38).
Figure 5:
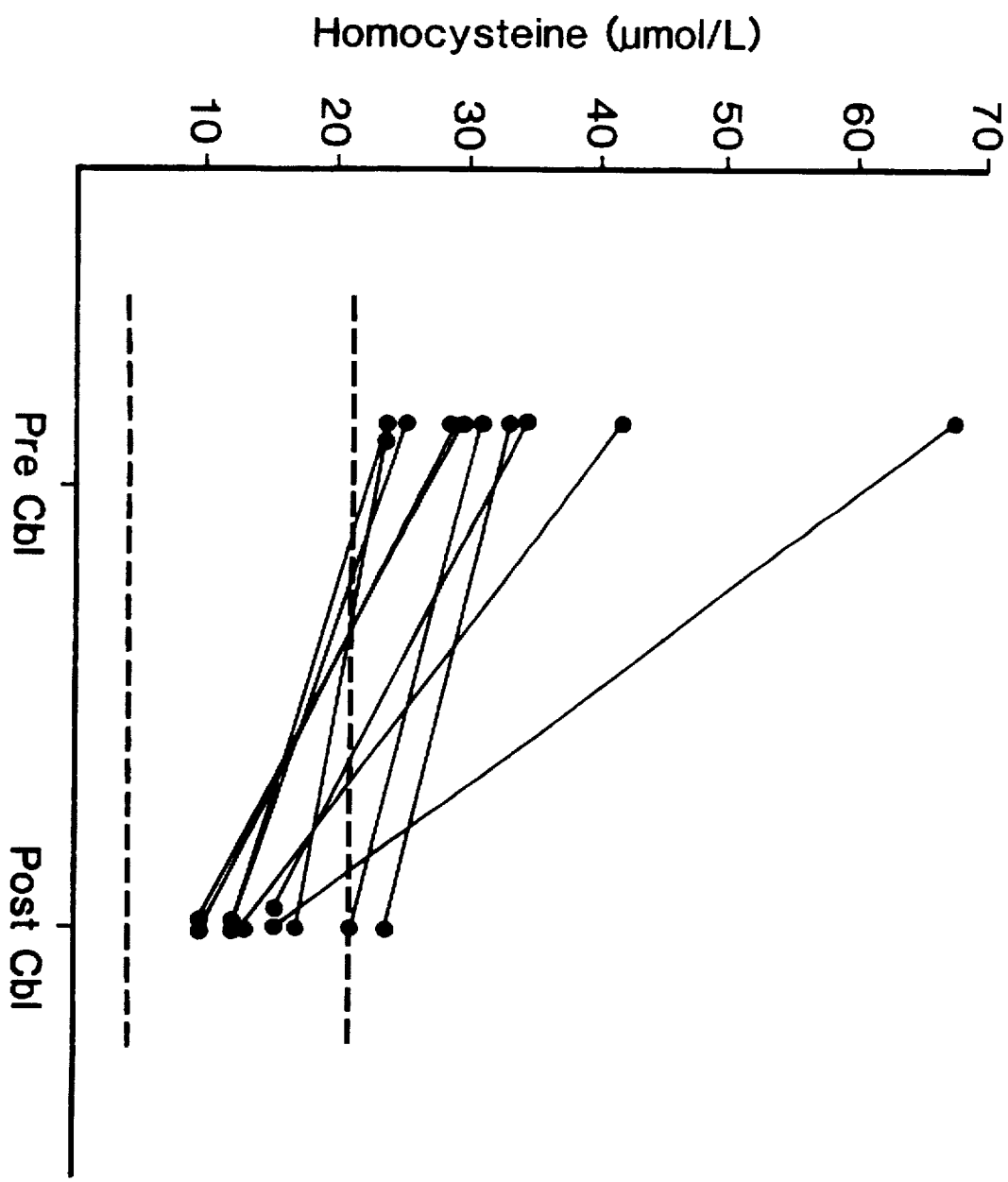
FIG. 5 shows serum HC levels before and after treatment with parenteral cobalamin for a population of elderly outpatients with elevated HC values and serum $B_{12}$ values of <300 pg/ml (ages 65–99, n=10/38).

Patients with low and low/normal serum $B_{12}$ levels were treated with weekly injections of 1.0 mg $B_{12}$. Parenteral $B_{12}$ administration caused elevated metabolite levels to fall to or towards normal (FIGS. 4 and 5) in every subject treated with $B_{12}$. It appears that the true prevalence of previously unrecognized $B_{12}$ deficiency in this elderly populations was at least 14.5%.

It can be seen from the data presented in Table 2 that serum $B_{12}$ levels are insensitive for screening $B_{12}$ deficiencies since similar numbers of patients with low normal serum $B_{12}$ levels of 201–300 pg/ml compared with patients with low $B_{12}$ levels (≦200 pg/ml) had markedly elevated metabolites which fell with $B_{12}$ treatment. Further, this study shows that elderly patients have a high incidence (at least 14.5%) of unrecognized $B_{12}$ deficiency, detectable by measurement of serum HC and MMA levels in patients with serum $B_{12}$ levels <300 pg/ml.

A further finding in this study emphasizes the need to treat elevated metabolite levels with a combination of vitamin $B_{12}$ and folate with or without $B_6$. Some of the patients exhibiting elevated metabolite levels did not fully respond to $B_{12}$ treatment. This may indicate a concomitant deficiency of folate and/or $B_6$. The lack of response to $B_{12}$ treatment could result from a deficiency of one, a pair, or all three vitamins. However, it would be expensive and time-consuming to attempt to distinguish between the vitamin deficiencies.

Another, and perhaps the most important, finding in this study is the large number of patients with serum $B_{12}$>300 pg/ml who have elevated values for one or more metabolites as indicated by a "**" next to the individual values. As can readily be seen in Table 2, there are many examples of elevated value for MMA and/or 2-MCA at all levels of serum $B_{12}$ including the mid-normal (300–600 pg/ml), the high-normal (600–800 pg/ml), and even the elevated (>800 pg/ml) ranges. The same is true for elevations of HC and CT. In some patients the serum folate is low, indicating that folate deficiency may be present, but in many cases both $B_{12}$ and folate levels are normal. $B_6$ levels were not performed in this study, but $B_6$ deficiency would not be expected to cause elevations of MMA or 2-MCA. Thus in many patients it is not clear which vitamin, or pair of vitamins, or whether all three vitamins is or are deficient. One could pick a single vitamin, often at random, with which to treat a patient for several weeks or months, and then repeat measurement of metabolite levels to determine if a partial or full correction had occurred. If there was no response, one could try another vitamin, or if there was a partial response one could add a second vitamin, and then repeat metabolite measurement after several weeks or months. If there was still no response, one could try the third vitamin, or if there was a partial response, one could try a different pair of vitamins. Eventually one could determine whether an individual vitamin, a particular pair of vitamins, or all three vitamins were required to normalize or maximally reduce the metabolite levels, but it would often require months or even a year to make this determination. Such a determination would be expensive. In addition, a patient who was optimally treated with a single vitamin or pair of vitamins might subsequently develop a deficiency of one or even two of the other vitamins as evidenced by a re-elevation or increase in the levels of one or more metabolites. Therapeutic testing could be reinitiated and continued as described above, although this would also be time-consuming and expensive.

It requires less time and expense to treat patients with elevated metabolite levels with a combination of vitamin $B_{12}$ and folate, or a combination of vitamin $B_{12}$ folate and vitamin $B_6$. The utility of the approach of the present invention is appreciated only after it is taught, for the first time in the present disclosure, that a deficiency of one or more of the three vitamins occurs commonly in the elderly population as evidenced by elevation of one or more metabolites, i.e., MMA, 2-MCA, HC and CT.

EXAMPLE 4.

Determination of Serum $B_{12}$, Folate, MMA, and HC Levels in a Geriatric Nursing Home Population.

Figure 6:
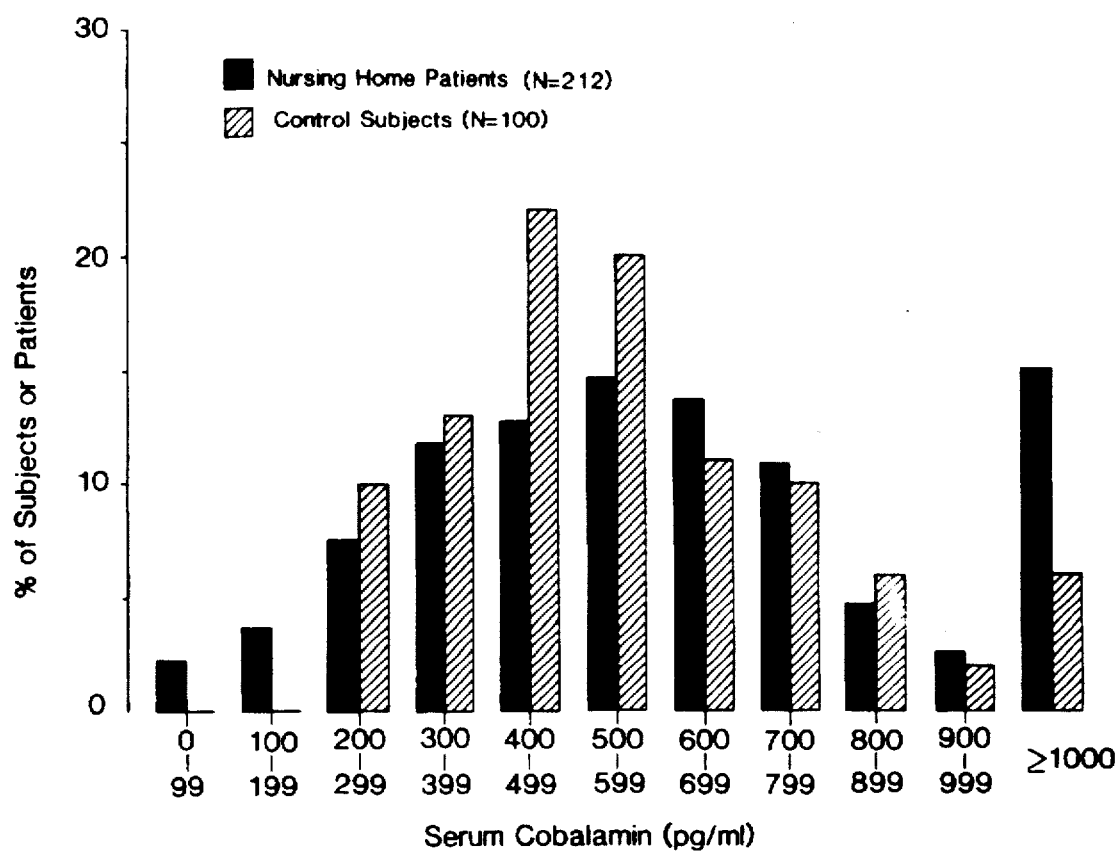
FIG. 6 shows the distribution of serum $B_{12}$ levels for a population of elderly nursing home patients (ages 55–107, n=212) and a normal population (ages 17–65, n=100).
Figure 7:
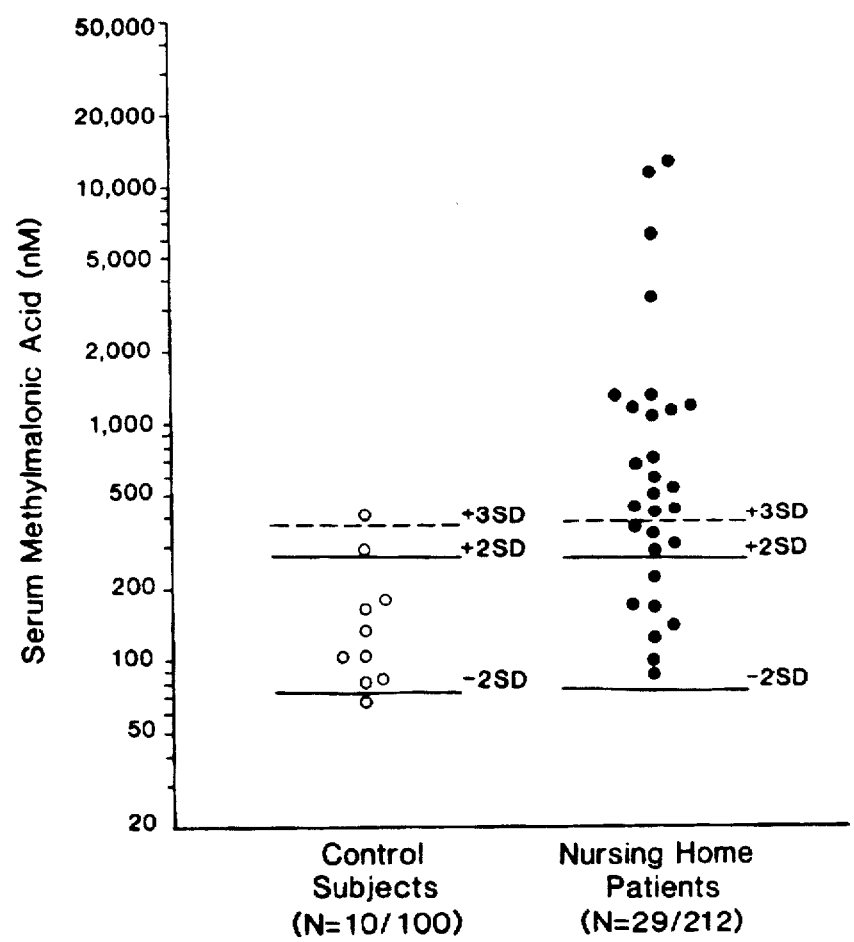
FIG. 7 shows serum MMA levels for a population of elderly nursing home patients with serum $B_{12}$ values <300 pg/ml (ages 55–107, n=29/212) and a normal population with serum $B_{12}$ values (ages 17–65, n=10/100).
Figure 8:
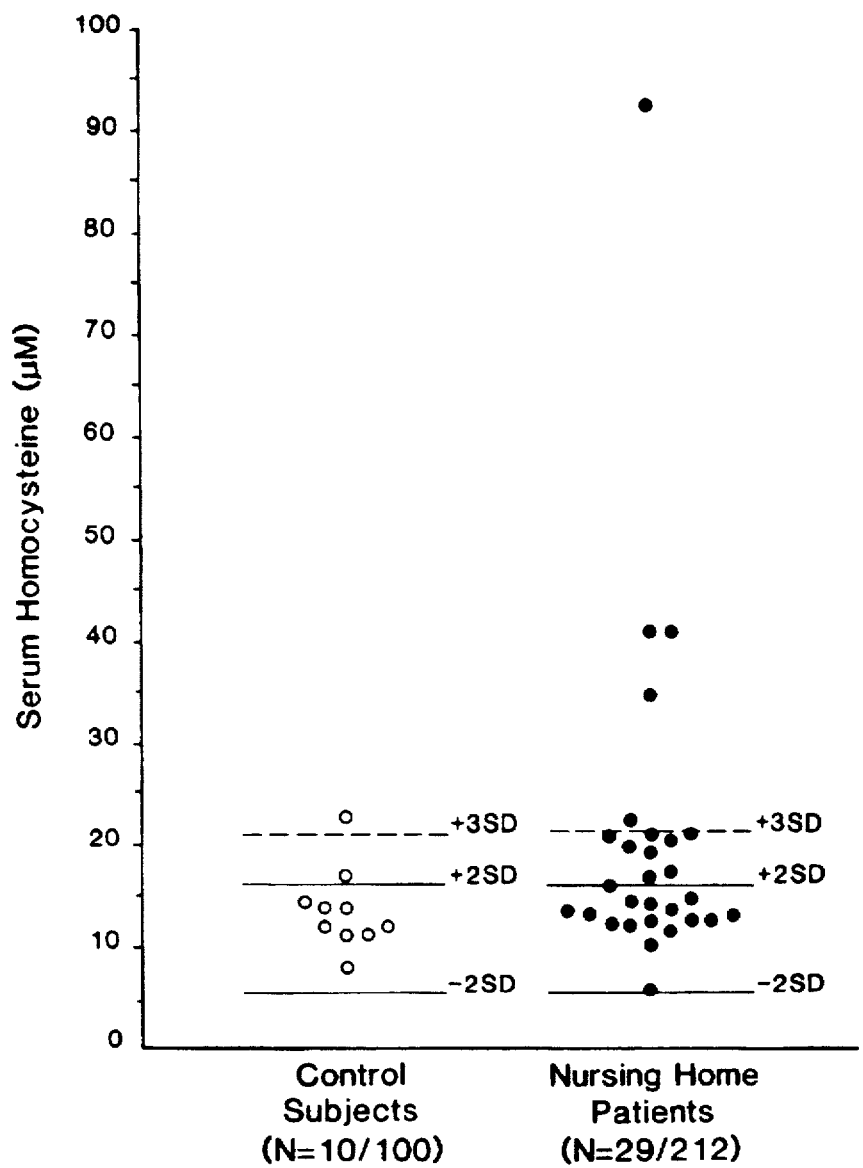
FIG. 8 shows serum HC levels for a population of elderly nursing home patients with serum $B_{12}$ values <300 pg/ml (ages 55–107, n=29/212) and a normal population with serum $B_{12}$ values <300 pg/ml (ages 17–65, n=10/100).
Figure 9:
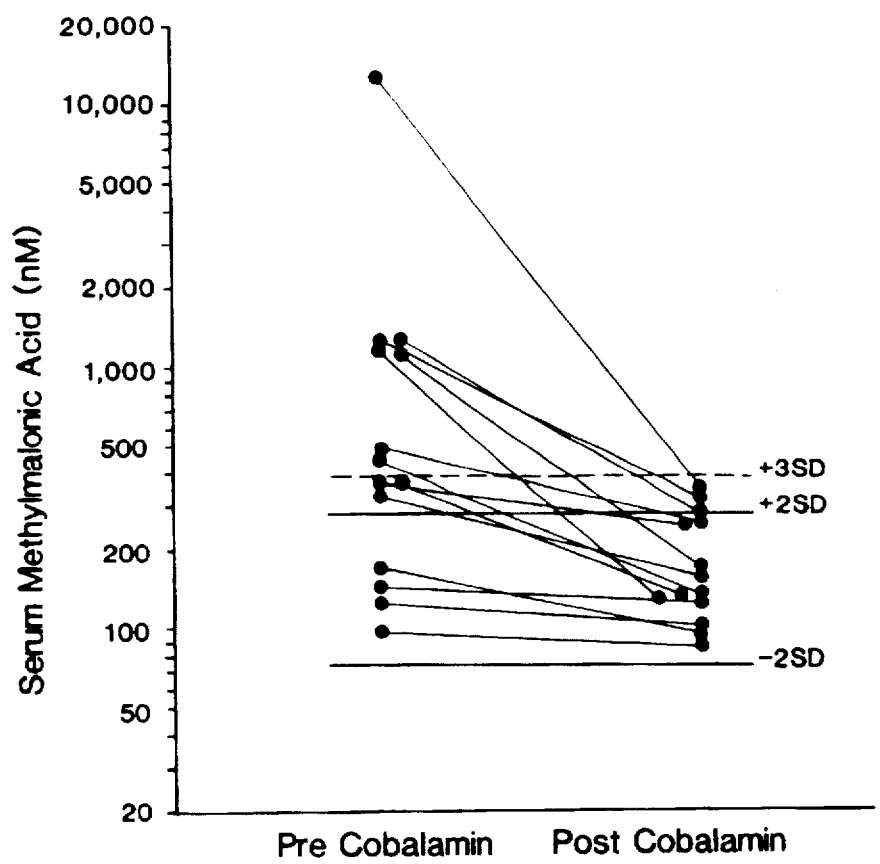
FIG. 9 shows serum MMA levels before and after treatment with parenteral cobalamin for a population of elderly nursing home patients with serum $B_{12}$ values <300 pg/ml (ages 55–107, n=14/29).
Figure 10:
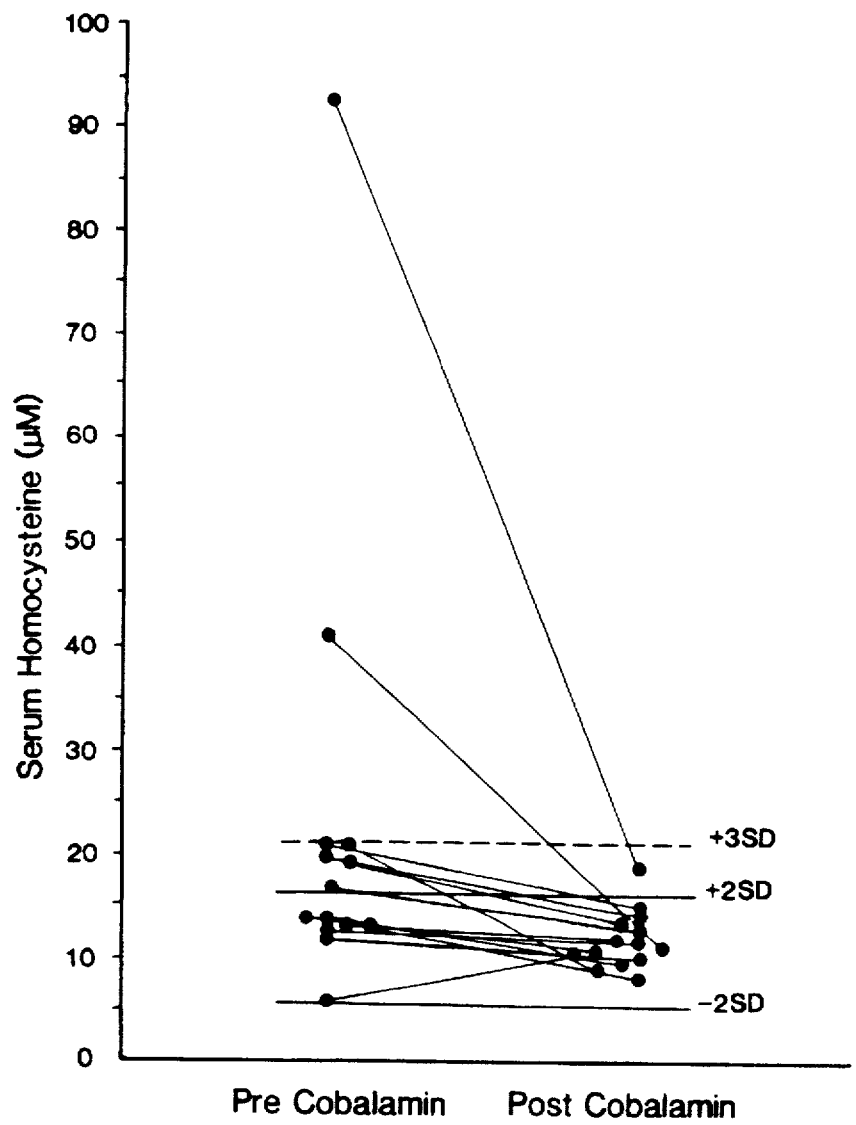
FIG. 10 shows serum HC levels before and after treatment with parenteral cobalamin for a population of elderly nursing home patients with serum $B_{12}$ values <300 pg/ml (ages 55–107, n=14/29).

A study was conducted with 212 elderly nursing home patients to determine serum $B_{12}$, folate, MMA, and HC levels (Table 3). The significance of the results shown in Table 3 marked with "**" are as described for Table 2 (Example 3). The control group consisted of 100 subjects between the ages of 17–65 years. As in the study described in Example 3, the elderly population exhibited a shift to lower serum $B_{12}$ levels (FIG. 6), elevated serum MMA (FIG. 7) and HC (FIG. 8) levels. Parenteral administration of $B_{12}$ 1 mg per week for 8 weeks to those with serum $B_{12}$ <300 pg/ml caused elevated MMA (FIG. 9) and HC (FIG. 10) levels to fall to or towards normal.

As in the study reported in Example 3, a further finding in this study emphasizes the need to treat elevated metabolite levels with a combination of vitamins $B_{12}$ and folate, with or without $B_6$. Some of the patients exhibiting elevated metabolite levels did not fully respond to $B_{12}$ treatment. This may indicate a concomitant deficiency of folate and/or $B_6$. The lack of response to $B_{12}$ treatment could result from a deficiency of one, a pair, or all three vitamins. However, it would be expensive and time-consuming to attempt to distinguish between the vitamin deficiencies.

Again, an important finding in this study is the large number of patients with serum $B_{12}$ >300 pg/ml who have elevated values for one or more metabolites as indicated by a "**" next to the individual values. As is seen in Table 3, there are many examples of elevated values for MMA at all levels of serum $B_{12}$ including the mid-normal (300–600 pg/ml), the high-normal (600–800 pg/ml), and even the elevated (>800 pg/ml) ranges. The same is true for elevations of HC. In some patients the serum folate is low, indicating that folate deficiency may be present, but in many cases both $B_{12}$ and folate levels are normal. $B_6$ levels were not performed in this study, but $B_6$ deficiency would not be expected to cause elevations of MMA. Thus, again it is not clear which vitamin, or pair of vitamins, or whether all three vitamins is or are deficient. One could pick a single vitamin with which to treat a patient for several weeks or months, and then repeat measurement of metabolite levels to determine if a partial or full correction had occurred. If there was no response, one could try another vitamin, or if there was a partial response one could add a second vitamin, and then repeat metabolite measurement after several weeks or months. If there was still no response, one could try the third vitamin, or if there was a partial response, one could try a different pair of vitamins. Eventually one could determine whether an individual vitamin, a particular pair of vitamins, or all three vitamins were required to normalize or maximally reduce the metabolite levels, but it would often require months or even a year to make this determination. Such a determination would be expensive. In addition, a patient who was optimally treated with a single vitamin or pair of vitamins might subsequently develop a deficiency of one or even two of the other vitamins as evidenced by a re-elevation or increase in the levels of one or more metabolites. Therapeutic testing could be reinitiated and continued as described above, although this would also be time-consuming and expensive.

It requires less time and expense to treat patients with elevated metabolite levels with a combination of vitamin $B_{12}$ and folate, or a combination of vitamin $B_{12}$, folate and vitamin $B_6$. The utility of the approach of the present invention is appreciated only after it is taught, for the first time in the present disclosure, that a deficiency of one or more of the three vitamins occurs commonly in the elderly population as evidenced by elevation of one or more metabolites, i.e., MMA, 2-MCA, HC and CT.

EXAMPLE 5.

Determination of Serum $B_{12}$, Folate, MMA, and HC Levels in a Geriatric Population.

A study was conducted with 548 elderly subjects from the Framingham study between the ages of 65–99 to determine serum $B_{12}$, folate, MMA, and HC levels (Table 4). The significance of the results shown in Table 4 (marked with "**") are as described for Table 2 (Example 2).

Figure 11:
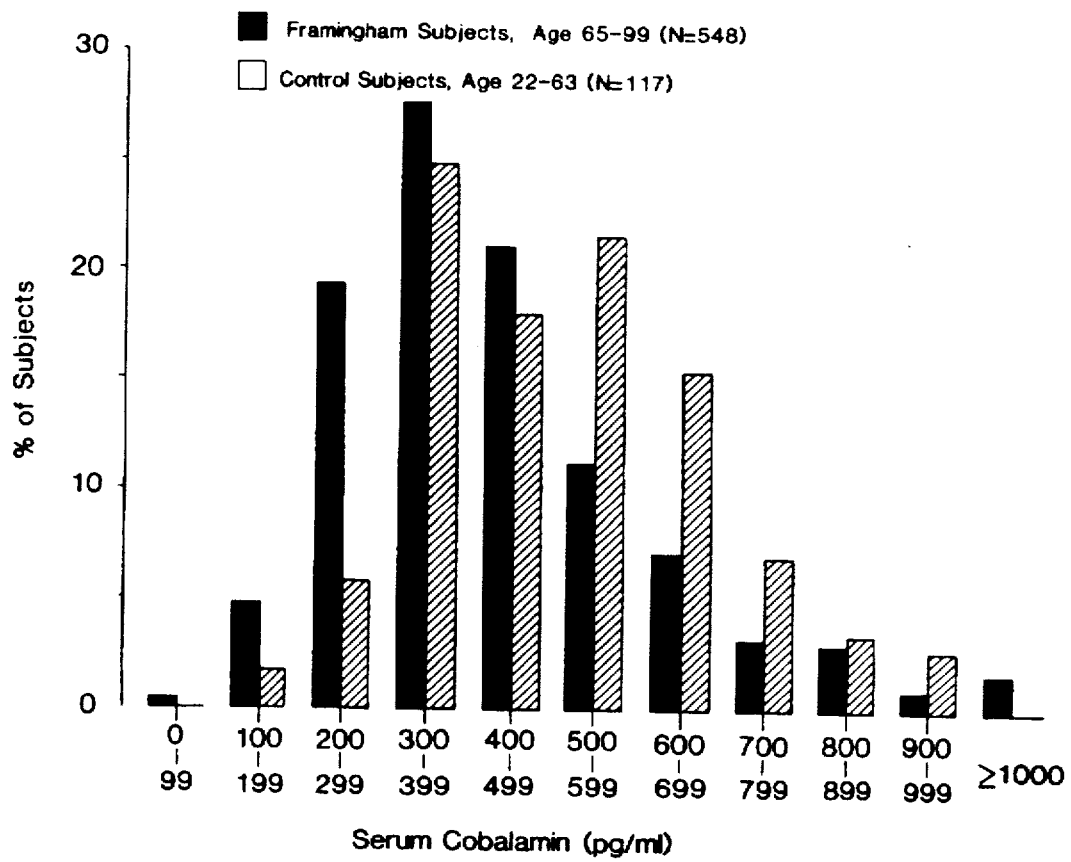
FIG. 11 shows the distribution of serum $B_{12}$ levels for a population of elderly patients (ages 65–99, n=548) and a normal population (ages 22–63, n=117) (Framingham study).

As in the study described in Examples 3 and 4, the elderly population exhibited a shift to lower serum $B_{12}$ levels (FIG. 11), and elevated serum MMA and HC levels. The elderly population also exhibited a high incidence (9.5%) of low serum folate levels (Table 4). As in the studies reported in Examples 2, 3 and 4, the incidence of tissue or intracellular vitamin deficiencies based on elevated metabolite levels was higher than that predicted from measurement of serum vitamin levels.

As in Examples 3 and 4 above, these results confirm the importance of the finding that there are a large number of patients with serum $B_{12}>300$ pg/ml who have elevated values for one or more metabolites as indicated by a "**" next to the individual values. As is seen in Table 4, there are many examples of elevated MMA values at all levels of serum $B_{12}$ including the mid-normal (300–600 pg/ml), the high-normal (600–800 pg/ml), and even the elevated (>800 pg/ml) ranges. The same is true for elevations of HC. In some patients the serum folate is low, indicating that folate deficiency may be present, but in many cases both $B_{12}$ and folate levels are normal. $B_6$ levels were not performed in this study, but $B_6$ deficiency would not be expected to cause elevations of MMA. Thus, again it is not clear which vitamin, or pair of vitamins, or whether all three vitamins is or are deficient. One could pick a single vitamin with which to treat a patient for several weeks or months, and then repeat measurement of metabolite levels to determine if a partial or full correction had occurred. If there was no response, one could try another vitamin, or if there was a partial response one could add a second vitamin, and then repeat metabolite measurement after several weeks or months. If there was still no response, one could try the third vitamin, or if there was a partial response, one could try a different pair of vitamins. Eventually one could determine whether an individual vitamin, a particular pair of vitamins, or all three vitamins were required to normalize or maximally reduce the metabolite levels, but it would often require months or even a year to make this determination. Such a determination would be expensive. In addition, a patient who was optimally treated with a single vitamin or pair of vitamins might subsequently develop a deficiency of one or even two of the other vitamins as evidenced by a re-elevation or increase in the levels of one or more metabolites. Therapeutic testing could be reinitiated and continued as described above, although this would also be time-consuming and expensive.

It requires less time and expense to treat patients with elevated metabolite levels with a combination of vitamin $B_{12}$ and folate, or a combination of vitamin $B_{12}$ folate and vitamin $B_6$. The utility of the approach of the present invention is appreciated only after it is taught, for the first time in the present disclosure, that a deficiency of one or more of the three vitamins occurs commonly in the elderly population as evidenced by elevation of one or more metabolites, i.e., MMA, 2-MCA, HC and CT.

TABLE 2

SERUM METABOLITE & VITAMIN LEVELS IN A GERIATRIC OUTPATIENT POPULATION.

| Patient | B12 | Folate | Homocysteine | MMA | CT | Total MC |
|---|---|---|---|---|---|---|
| 116 | 66** | 9.8 | 41.8** | 1508** | 507** | 759** |
| 118 | 79** | 9.3 | 29.6** | 2200** | 343** | 428** |
| 016 | 155** | 7.6 | 15.3 | 1316** | 208 | 196 |
| 067 | 163** | 6.6 | 9.9 | 93 | 164 | 69 |
| 091 | 178** | 12.0 | 29.2** | 3108** | 438** | 318** |
| 042 | 181** | 11.3 | 13.0 | 452** | 300 | 262** |
| 030 | 185** | 6.6 | 26.0** | 282** | 310 | 223 |
| 037 | 187** | 9.4 | 12.3 | 160 | 218 | 334** |
| 100 | 187** | 9.5 | 13.6 | 208 | 453** | 141 |
| 036 | 188** | 9.9 | 16.3** | 298** | 385** | 322** |
| 109 | 189** | 7.6 | 12.3 | 127 | 188 | 161 |
| 007 | 191** | 11.7 | 67.1** | 6349** | 619** | 1005** |
| 018 | 193** | 5.8 | 16.7** | 412** | 272 | 235** |
| 050 | 210 | 4.0 | 25.3** | 464** | 727** | 121 |
| 108 | 214 | 6.0 | 31.1** | 264 | 523** | 315** |
| 041 | 216 | 7.2 | 19.1** | 418** | 360** | 288** |
| 126 | 224 | 6.5 | 8.8 | 103 | 361** | 121 |
| 005 | 231 | 12.5 | 17.1** | 269 | 825** | 276** |
| 024 | 235 | 13.0 | 18.5** | 2946** | 232 | 289** |
| 111 | 237 | 6.3 | 14.6 | 135 | 380** | 203 |
| 023 | 239 | 4.1 | 21.9** | 385** | 775** | 279** |
| 010 | 256 | 12.9 | 11.5 | 652** | 119 | 144 |
| 055 | 258 | 6.8 | 7.5 | 189 | 342 | 185 |
| 102 | 259 | 10.9 | 23.9** | 1894** | 423** | 400** |
| 026 | 260 | 18.5 | 20.4** | 1949** | 295 | 248** |
| 107 | 262 | 13.1 | 10.1 | 231 | 628** | 153 |
| 038 | 269 | 7.6 | 15.7 | 222 | 152 | 152 |
| 140 | 277 | 4.0 | 29.1** | 744** | 602** | 254** |
| 074 | 278 | 5.2 | 24.1** | 699** | 296 | 187 |
| 002 | 278 | 14.6 | 14.8 | 554** | 259 | 277** |
| 019 | 282 | 8.5 | 12.4 | 329** | 262 | 161 |
| 035 | 287 | 5.8 | 9.8 | 230 | 390** | 218 |
| 049 | 290 | 3.9 | 33.0** | 140 | 275 | 138 |
| 078 | 290 | 10.9 | 12.5 | 197 | 240 | 209 |
| 045 | 291 | 8.7 | 9.5 | 162 | 613** | 132 |
| 092 | 294 | 14.9 | 19.3** | 500** | 246 | 167 |
| 137 | 297 | 6.8 | 10.1 | 631** | 340 | 184 |
| 072 | 298 | 6.7 | 19.7** | 375** | 302 | 246** |
| 149 | 310 | 8.3 | 16.1 | 314** | 199 | 149 |
| 047 | 312 | 4.9 | 15.9 | 277** | 271 | 173 |
| 060 | 312 | 9.4 | 8.0 | 100 | 228 | 203 |
| 046 | 314 | 6.5 | 16.2 | 142 | 336 | 125 |
| 093 | 318 | 6.4 | 16.5** | 304** | 361** | 130 |
| 014 | 321 | 14.5 | 10.7 | 275** | 233 | 170 |

TABLE 2-continued

SERUM METABOLITE & VITAMIN LEVELS IN A GERIATRIC OUTPATIENT POPULATION.

| Patient | B12 | Folate | Homocysteine | MMA | CT | Total MC |
|---|---|---|---|---|---|---|
| 088 | 327 | 7.1 | 17.8** | 263 | 507** | 258** |
| 032 | 340 | 6.6 | 8.6 | 150 | 133 | 133 |
| 147 | 347 | 7.6 | 18.2** | 305** | 219 | 265** |
| 001 | 351 | 4.7 | 20.8** | 199 | 402** | 223 |
| 090 | 353 | 4.9 | 20.7** | 144 | 419** | 178 |
| 008 | 358 | 5.4 | 11.6 | 372** | 529** | 177 |
| 104 | 360 | 12.7 | 12.1 | 260 | 89 | 77 |
| 110 | 370 | 3.0** | 17.1** | 456** | 297 | 150 |
| 103 | 371 | 18.7 | 14.5 | 257 | 219 | 180 |
| 056 | 373 | 6.5 | 12.4 | 236 | 415** | 189 |
| 048 | 374 | 3.6** | 9.7 | 167 | 237 | 230** |
| 131 | 377 | 10.9 | 13.6 | 256 | 220 | 85 |
| 122 | 378 | 7.6 | 21.9** | 906** | 227 | 196 |
| 004 | 385 | 8.6 | 10.3 | 109 | 288 | 92 |
| 120 | 390 | 9.8 | 22.9** | 499** | 529** | 260** |
| 138 | 405 | 6.9 | 14.7 | 334** | 238 | 188 |
| 141 | 407 | 8.1 | 14.3 | 168 | 259 | 263** |
| 101 | 408 | 5.9 | 9.2 | 160 | 134 | 40 |
| 145 | 410 | 3.7** | 25.4** | 567** | 550** | 349** |
| 027 | 415 | 11.1 | 10.6 | 169 | 278 | 164 |
| 028 | 418 | 5.6 | 34.6** | 608** | 589** | 351** |
| 011 | 420 | 10.6 | 18.8** | 683** | 1014** | 282** |
| 081 | 421 | 6.6 | 16.5** | 861** | 641** | 531** |
| 033 | 423 | 4.2 | 16.3** | 156 | 194 | 170 |
| 057 | 425 | 18.3 | 13.5 | 209 | 381** | 321** |
| 021 | 427 | 18.9 | 12.1 | 223 | 524** | 168 |
| 135 | 430 | 8.8 | 13.5 | 284** | 412** | 180 |
| 097 | 435 | 15.4 | 10.9 | 353** | 465** | 119 |
| 052 | 438 | 6.8 | 15.2 | 281** | 372** | 238** |
| 132 | 448 | 12.6 | 16.8** | 1931** | 394** | 250** |
| 086 | 451 | 12.1 | 6.6 | 139 | 208 | 107 |
| 148 | 458 | 13.9 | 11.4 | 187 | 322 | 238** |
| 012 | 466 | 15.3 | 8.3 | 560** | 250 | 144 |
| 083 | 466 | 12.0 | 13.7 | 366** | 214 | 193 |
| 133 | 470 | 13.8 | 10.8 | 290** | 275 | 55 |
| 017 | 475 | 4.0 | 39.6** | 196 | 467** | 220 |
| 053 | 476 | 13.4 | 12.3 | 226 | 206 | 125 |
| 009 | 482 | 6.5 | 25.3** | 240 | 470** | 214 |
| 066 | 498 | 9.6 | 12.9 | 374** | 233 | 92 |
| 031 | 507 | 11.0 | 14.8 | 173 | 278 | 220 |
| 099 | 507 | 10.4 | 9.6 | 124 | 233 | 63 |
| 128 | 507 | 4.6 | 9.4 | 294** | 324 | 176 |
| 013 | 514 | 11.3 | 15.9 | 163 | | |
| 151 | 522 | 7.8 | 14.3 | 370** | 324 | 215 |
| 077 | 523 | 6.8 | 17.7** | 184 | 210 | 214 |
| 079 | 523 | 15.6 | 13.0 | 316** | 223 | 251** |
| 054 | 524 | 4.9 | 10.0 | 148 | 230 | 123 |
| 020 | 524 | 9.9 | 14.2 | 235 | 366** | 190 |
| 069 | 528 | 7.0 | 9.7 | 257 | 281 | 83 |
| 085 | 536 | 4.0 | 22.5** | 97 | 191 | 114 |
| 084 | 551 | 14.2 | 12.5 | 166 | 179 | 131 |
| 082 | 559 | 12.3 | 14.6 | 208 | 371** | 182 |
| 117 | 560 | 3.4** | 18.8** | 102 | 176 | 88 |
| 061 | 561 | 12.7 | 9.8 | 170 | 404** | 152 |
| 006 | 567 | 4.6 | 16.8** | 138 | 688** | 165 |
| 129 | 567 | 4.9 | 16.2 | 363** | 495** | 331** |
| 003 | 570 | 11.4 | 12.9 | 189 | 330 | 230** |
| 115 | 576 | 6.3 | 17.8* * | 128 | 231 | 95 |
| 089 | 578 | 10.3 | 12.0 | 147 | 258 | 236** |
| 143 | 581 | 2.6** | 42.7** | 165 | 555** | 208 |
| 114 | 583 | 5.1 | 16.6** | 599** | 660** | 177 |
| 080 | 593 | 9.5 | 18.0** | 208 | 289 | 142 |
| 015 | 598 | 7.0 | 12.4 | 167 | 381** | 95 |
| 039 | 598 | 9.6 | 18.1** | 691** | 719** | 354** |
| 070 | 612 | 5.6 | 13.7 | 197 | 296 | 82 |
| 051 | 622 | 12.9 | 8.3 | 119 | 246 | 150 |
| 139 | 628 | 8.5 | 7.8 | 145 | 166 | 83 |
| 150 | 628 | 8.6 | 14.5 | 295** | 315 | 183 |
| 043 | 635 | 5.9 | 13.7 | 239 | 272 | 189 |
| 096 | 651 | 17.4 | 9.7 | 326** | | |
| 073 | 657 | 7.0 | 9.5 | 186 | 283 | 78 |
| 127 | 665 | 5.8 | 8.1 | 166 | 344** | 147 |
| 121 | 677 | 10.2 | 9.5 | 226 | 346** | 173 |
| 034 | 694 | 15.9 | 12.1 | 406** | 592** | 584** |

TABLE 2-continued

SERUM METABOLITE & VITAMIN LEVELS IN A GERIATRIC OUTPATIENT POPULATION.

| Patient | B12 | Folate | Homocysteine | MMA | CT | Total MC |
|---|---|---|---|---|---|---|
| 124 | 697 | 9.7 | 11.0 | 63 | 179 | 60 |
| 123 | 702 | 10.4 | 10.6 | 186 | 148 | 96 |
| 113 | 705 | 7.6 | 8.4 | 107 | 534** | 92 |
| 071 | 709 | 10.6 | 11.3 | 207 | 584** | 141 |
| 076 | 722 | 8.1 | 10.5 | 271 | 489** | 138 |
| 044 | 724 | 7.3 | 12.1 | 212 | 683** | 217 |
| 040 | 731 | 15.1 | 7.4 | 205 | 149 | 136 |
| 062 | 741 | 4.4 | 18.7** | 153 | 856** | 416** |
| 025 | 741 | 10.0 | 12.2 | 224 | 344** | 121 |
| 119 | 755 | 5.9 | 10.1 | 187 | 377** | 61 |
| 075 | 757 | 10.0 | 24.7** | 246 | 345** | 276** |
| 098 | 759 | 13.8 | 13.9 | 380** | 239 | 156 |
| 134 | 769 | 7.5 | 10.4 | 125 | 131 | 81 |
| 087 | 773 | 25.0 | 10.1 | 181 | 285 | 135 |
| 142 | 788 | 4.6 | 12.1 | 166 | 273 | 129 |
| 064 | 792 | 15.4 | 8.6 | 218 | 299 | 139 |
| 094 | 793 | 16.6 | 10.0 | 186 | 179 | 173 |
| 022 | 808 | 8.8 | 14.4 | 184 | 271 | 161 |
| 112 | 812 | 12.0 | 9.2 | 181 | 184 | 108 |
| 125 | 817 | 14.4 | 11.0 | 158 | 242 | 72 |
| 106 | 862 | 5.3 | 9.2 | 94 | 300 | 95 |
| 146 | 890 | 13.9 | 11.9 | 135 | | |
| 058 | 897 | 5.3 | 18.5** | 154 | 460** | 80 |
| 063 | 943 | 17.8 | 19.7** | 277** | 642** | 306** |
| 095 | 960 | 25.3 | 10.7 | 135 | 181 | 111 |
| 152 | 963 | 9.4 | 8.8 | 198 | | |
| 130 | 971 | 15.9 | 13.5 | 106 | 307 | 84 |
| 059 | 1063 | 9.4 | 9.7 | 129 | 378** | 54 |
| 105 | 1109 | 11.0 | 6.1 | 87 | 155 | 64 |
| 136 | 1163 | 6.0 | 13.1 | 250 | 565** | 122 |
| 065 | 1251 | 14.5 | 10.7 | 88 | 147 | 88 |
| 029 | 1490 | 22.2 | 9.7 | 129 | 111 | 105 |
| 144 | 1536 | 7.0 | 17.7** | 216 | 694** | 418** |
| 068 | 1809 | 12.7 | 10.4 | 59 | 128 | 39 |

TABLE 3

SERUM METABOLITE & VITAMIN LEVELS IN A GERIATRIC NURSING HOME POPULATION.

| Patient | B12 | Folate | Homocysteine | Methylmalonic Acid |
|---|---|---|---|---|
| NH170 | 8** | 14.0 | 34.8** | 3365** |
| NH129 | 40** | 7.4 | 40.9** | 6245** |
| NH156 | 44** | 22.4 | 17.4** | 1130** |
| NH139 | 56** | 9.7 | 20.9** | 1180** |
| NH132 | 67** | 7.6 | 92.4** | 12641** |
| NH176 | 129** | 9.2 | 20.3** | 1156** |
| NH196 | 136** | 6.2 | 41.0** | 1077** |
| NH109 | 139** | 9.8 | 20.9** | 1294** |
| NH203 | 146** | 4.3 | 12.2 | 437** |
| NH141 | 161** | 13.4 | 12.2 | 223 |
| NH178 | 172** | 8.2 | 5.9 | 141 |
| NH103 | 189** | 5.5 | 13.1 | 362** |
| NH181 | 196** | 6.3 | 14.7 | 296** |
| NH160 | 206 | 11.9 | 12.5 | 640** |
| NH197 | 221 | 24.0 | 10.5 | 654** |
| NH073 | 222 | 3.6** | 19.8** | 490** |
| NH110 | 227 | 5.5 | 13.7 | 1297** |
| NH010 | 228 | 4.0 | 21.1** | 413** |
| NH012 | 234 | 8.7 | 16.0 | 596** |
| NH037 | 236 | 11.5 | 22.5** | 11299** |
| NH114 | 238 | 12.8 | 13.2 | 442** |
| NH211 | 240 | 6.0 | 14.1 | 166 |
| NH075 | 250 | 9.3 | 12.1 | 170 |
| NH172 | 255 | 7.2 | 14.4 | 552** |
| NH148 | 259 | 5.7 | 19.2** | 317** |
| NH138 | 264 | 9.2 | 16.7** | 340** |
| NH150 | 264 | 4.0 | 13.7 | 98 |
| NH099 | 272 | 5.5 | 12.5 | 125 |
| NH124 | 275 | 6.9 | 11.5 | 87 |
| NH179 | 301 | 7.6 | 7.1 | 143 |
| NH135 | 302 | 6.5 | 23.4** | 397** |
| NH087 | 304 | 7.8 | 10.8 | 327** |
| NH180 | 304 | 5.8 | 10.5 | 237 |
| NH209 | 306 | 7.6 | 11.9 | 105 |
| NH107 | 310 | 3.3** | 8.6 | 148 |
| NH081 | 320 | 4.3 | 23.6** | 470** |
| NH068 | 324 | 7.9 | 13.4 | 243 |
| NH183 | 325 | 7.7 | 11.1 | 144 |
| NH033 | 330 | 13.8 | 7.7 | 149 |
| NH161 | 333 | 8.5 | 11.3 | 385** |
| NH192 | 337 | 10.7 | 9.5 | 209 |
| NH136 | 340 | 6.7 | 18.2** | 409** |
| NH191 | 342 | 20.2 | 13.4 | 271 |
| NH137 | 343 | 4.0 | 15.6 | 183 |
| NH182 | 346 | 8.2 | 14.4 | 448** |
| NH020 | 347 | 8.4 | 10.4 | 149 |
| NH165 | 351 | 18.5 | 11.8 | 425** |
| NH095 | 352 | 8.5 | 14.5 | 366** |
| NH194 | 361 | 4.3 | 20.3** | 305** |
| NH106 | 362 | 4.8 | 12.9 | 298** |
| NH060 | 367 | 4.7 | 16.4** | 71 |
| NH009 | 368 | 5.1 | 15.9 | 325** |
| NH071 | 382 | 4.9 | 12.9 | 330** |
| NH080 | 390 | 6.1 | 15.0 | 171 |
| NH013 | 407 | 6.7 | 12.4 | 310** |
| NH126 | 409 | 9.2 | 17.4** | 137 |

TABLE 3-continued

SERUM METABOLITE & VITAMIN LEVELS IN A GERIATRIC NURSING HOME POPULATION.

| Patient | B12 | Folate | Homocysteine | Methylmalonic Acid |
|---|---|---|---|---|
| NH030 | 411 | 11.2 | 10.4 | 844** |
| NH210 | 413 | 8.6 | 11.9 | 210 |
| NH158 | 414 | 5.7 | 16.2 | 508** |
| NH027 | 416 | 10.2 | 15.5 | 769** |
| NH003 | 424 | 16.5 | 9.5 | 167 |
| NH187 | 429 | 4.7 | 8.8 | 439** |
| NH022 | 430 | 10.5 | 14.0 | 214 |
| NH082 | 436 | 10.6 | 17.7** | 340** |
| NH162 | 438 | 6.1 | 19.2** | 180 |
| NH021 | 439 | 5.3 | 15.1 | 191 |
| NH056 | 447 | 11.7 | 10.9 | 184 |
| NH119 | 448 | 3.2** | 14.1 | 241 |
| NH120 | 448 | 5.6 | 12.0 | 138 |
| NH186 | 450 | 4.7 | 23.1** | 213 |
| NH064 | 451 | 6.9 | 10.6 | 237 |
| NH057 | 453 | 14.6 | 10.4 | 282** |
| NH131 | 454 | 8.1 | 16.2 | 258 |
| NH059 | 462 | 6.0 | 9.1 | 147 |
| NH202 | 465 | 3.3** | 17.0** | 393** |
| NH134 | 475 | 15.3 | 11.6 | 321** |
| NH083 | 475 | 7.4 | 10.6 | 178 |
| NH199 | 479 | 15.1 | 10.4 | 141 |
| NH042 | 482 | 6.0 | 15.0 | 141 |
| NH200 | 491 | 13.6 | 9.8 | 154 |
| NH213 | 497 | 8.1 | 10.0 | 92 |
| NH143 | 500 | 5.2 | 22.1** | 175 |
| NH031 | 502 | 6.4 | 16.1 | 151 |
| NH188 | 504 | 12.5 | 15.1 | 1461** |
| NH171 | 504 | 10.7 | 12.9 | 344** |
| NH008 | 505 | 4.6 | 9.9 | 185 |
| NH102 | 506 | 16.6 | 9.1 | 236 |
| NH145 | 512 | 7.7 | 22.2** | 161 |
| NH093 | 514 | 5.1 | 17.7** | 185 |
| NH118 | 524 | 25.0 | 10.1 | 314** |
| NH185 | 524 | 8.7 | 12.1 | 84 |
| NH111 | 527 | 5.1 | 18.4** | 250 |
| NH149 | 530 | 12.6 | 18.2** | 531** |
| NH011 | 534 | 8.1 | 12.5 | 654** |
| NH128 | 540 | 4.3 | 11.6 | 120 |
| NH035 | 547 | 7.5 | 9.8 | 193 |
| NH005 | 551 | 17.7 | 5.0 | 365** |
| NH212 | 552 | 11.9 | 12.1 | 202 |
| NH007 | 554 | 6.4 | 26.1** | 646** |
| NH086 | 554 | 9.5 | 5.1 | 127 |
| NH069 | 555 | 22.7 | 6.8 | 134 |
| NH121 | 555 | 8.2 | 10.0 | 112 |
| NH117 | 571 | 6.6 | 9.7 | 351** |
| NH055 | 581 | 14.8 | 9.1 | 265 |
| NH025 | 581 | 5.2 | 15.3 | 181 |
| NH104 | 583 | 3.9 | 14.6 | 1699** |
| NH173 | 583 | 11.2 | 10.6 | 160 |
| NH177 | 584 | 6.2 | 5.7 | 111 |
| NH207 | 586 | 8.5 | 16.4** | 243 |
| NH070 | 591 | 5.4 | 12.0 | 168 |
| NH038 | 592 | 8.0 | 8.8 | 230 |
| NH049 | 599 | 10.7 | 21.7** | 238 |
| NH062 | 606 | 4.5 | 7.7 | 96 |
| NH153 | 608 | 7.7 | 13.6 | 221 |
| NH206 | 611 | 6.6 | 16.4** | 400** |
| NH018 | 614 | 6.3 | 10.9 | 123 |
| NH163 | 616 | 5.0 | 9.6 | 132 |
| NH189 | 619 | 7.6 | 12.0 | 158 |
| NH045 | 620 | 21.0 | 12.4 | 265 |
| NH074 | 621 | 10.2 | 9.2 | 172 |
| NH054 | 623 | 8.0 | 9.8 | 121 |
| NH152 | 625 | 8.2 | 7.8 | 206 |
| NH140 | 637 | 21.7 | 13.6 | 300** |
| NH050 | 642 | 16.3 | 13.5 | 275** |
| NH089 | 644 | 7.7 | 16.7** | 444** |
| NH036 | 649 | 7.9 | 10.7 | 68 |
| NH097 | 651 | 6.6 | 13.4 | 426** |
| NH016 | 656 | 4.1 | 61.0** | 356** |
| NH053 | 657 | 14.2 | 10.6 | 320** |
| NH066 | 658 | 7.7 | 11.4 | 228 |
| NH051 | 659 | 4.0 | 10.7 | 216 |
| NH108 | 671 | 5.8 | 24.0** | 823** |
| NH058 | 673 | 6.0 | 11.2 | 392** |
| NH028 | 675 | 22.3 | 9.1 | 105 |
| NH204 | 678 | 4.7 | 10.2 | 148 |
| NH169 | 679 | 6.9 | 19.2** | 267 |
| NH032 | 681 | 12.7 | 5.9 | 99 |
| NH065 | 682 | 11.0 | 13.5 | 176 |
| NH061 | 683 | 13.4 | 9.6 | 190 |
| NH116 | 685 | 9.0 | 7.5 | 244 |
| NH015 | 699 | 6.8 | 16.8** | 236 |
| NH157 | 711 | 10.0 | 12.8 | 198 |
| NH155 | 715 | 10.0 | 17.6** | 308** |
| NH034 | 715 | 7.9 | 11.4 | 179 |
| NH040 | 717 | 10.5 | 15.7 | 256 |
| NH105 | 718 | 6.0 | 13.2 | 308** |
| NH048 | 719 | 8.0 | 10.8 | 207 |
| NH084 | 720 | 6.8 | 9.4 | 169 |
| NH115 | 724 | 16.3 | 9.4 | 161 |
| NH205 | 734 | 8.5 | 13.3 | 232 |
| NH113 | 738 | 11.7 | 10.3 | 171 |
| NH154 | 738 | 13.7 | 9.6 | 123 |
| NH167 | 741 | 17.0 | 6.6 | 129 |
| NH190 | 752 | 5.2 | 14.1 | 254 |
| NH067 | 760 | 22.5 | 9.5 | 232 |
| NH014 | 767 | 8.9 | 7.3 | 100 |
| NH072 | 768 | 8.3 | 6.9 | 131 |
| NH133 | 772 | 8.8 | 20.4** | 219 |
| NH122 | 778 | 6.0 | 10.4 | 108 |
| NH076 | 781 | 12.1 | 14.9 | 282** |
| NH147 | 785 | 7.5 | 24.5** | 411** |
| NH026 | 786 | 9.7 | 8.3 | 146 |
| NH151 | 789 | 24.4 | 11.1 | 182 |
| NH198 | 797 | 10.9 | 10.7 | 158 |
| NH088 | 801 | 6.4 | 18.3** | 184 |
| NH004 | 806 | 11.3 | 8.8 | 96 |
| NH024 | 818 | 5.1 | 14.1 | 219 |
| NH100 | 826 | 16.4 | 10.5 | 103 |
| NH078 | 831 | 7.2 | 10.3 | 266 |
| NH052 | 844 | 19.6 | 8.0 | 193 |
| NH142 | 848 | 18.6 | 12.1 | 398** |
| NH002 | 862 | 9.4 | 11.3 | 212 |
| NH091 | 891 | 4.9 | 12.6 | 169 |
| NH127 | 897 | 22.0 | 8.4 | 132 |
| NH096 | 901 | 9.3 | 5.2 | 104 |
| NH201 | 910 | 25.0 | 15.7 | 424** |
| NH184 | 941 | 21.5 | 10.8 | 170 |
| NH208 | 945 | 20.2 | 9.8 | 111 |
| NH130 | 968 | 22.4 | 10.4 | 339** |
| NH164 | 989 | 8.0 | 16.8** | 102 |
| NH077 | 1006 | 15.1 | 9.2 | 188 |
| NH017 | 1015 | 11.9 | 9.5 | 175 |
| NH029 | 1053 | 18.6 | 11.4 | 161 |
| NH023 | 1055 | 9.3 | 9.7 | 193 |
| NH047 | 1079 | 6.4 | 11.4 | 106 |
| NH043 | 1082 | 14.5 | 13.9 | 144 |
| NH195 | 1088 | 36.9 | 12.2 | 150 |
| NH193 | 1092 | 8.2 | 15.7 | 225 |
| NH046 | 1093 | 9.2 | 18.8** | 186 |
| NH101 | 1108 | 3.9 | 8.1 | 139 |
| NH098 | 1117 | 11.3 | 12.5 | 88 |
| NH168 | 1124 | 25.2 | 15.0 | 203 |
| NH006 | 1126 | 6.9 | 8.1 | 159 |
| NH144 | 1135 | 8.0 | 21.9** | 262 |
| NH044 | 1159 | 26.8 | 10.2 | 109 |
| NH175 | 1162 | 7.8 | 12.0 | 210 |
| NH146 | 1179 | 9.8 | 10.1 | 129 |
| NH112 | 1238 | 10.3 | 15.0 | 347** |
| NH001 | 1304 | 13.1 | 6.9 | 142 |
| NH166 | 1337 | 13.4 | 8.3 | 67 |
| NH079 | 1346 | 18.0 | 12.0 | 248 |
| NH041 | 1528 | 20.7 | 8.2 | 155 |
| NH063 | 1559 | 15.0 | 7.0 | 66 |
| NH159 | 1566 | 6.6 | 15.5 | 451** |

TABLE 3-continued

SERUM METABOLITE & VITAMIN LEVELS IN A GERIATRIC NURSING HOME POPULATION.

| Patient | B12 | Folate | Homocysteine | Methylmalonic Acid |
|---|---|---|---|---|
| NH125 | 1703 | 8.2 | 20.6** | 153 |
| NH094 | 1768 | 15.9 | 8.4 | 182 |
| NH123 | 2028 | 10.2 | 16.8** | 206 |
| NH174 | 2106 | 13.3 | 12.8 | 280** |
| NH039 | 2227 | 23.8 | 8.9 | 119 |
| NH019 | 2297 | 11.1 | 15.5 | 177 |
| NH092 | 2360 | 5.7 | 9.8 | 131 |
| NH085 | 3141 | 22.0 | 26.9** | 1947** |

TABLE 4

SERUM METABOLITE AND VITAMIN LEVELS IN A GERIATRIC POPULATION.

| Patient | $B_{12}$ | Folate | Homocysteine | MMA |
|---|---|---|---|---|
| 495 | 77** | 10.0 | 65.4** | 3145** |
| 484 | 84** | 10.0 | 77.5** | 6820** |
| 522 | 100** | 3.6** | 15.5 | 967** |
| 455 | 115** | 1.9** | 21.8** | 170 |
| 493 | 135** | 4.4 | 16.9** | 421** |
| 528 | 145** | 3.9 | 38.3** | 729** |
| 510 | 155** | 4.6 | 14.1 | 804** |
| 502 | 155** | 2.1** | 16.9** | 347** |
| 412 | 160** | 18.5 | 33.8** | 1301** |
| 409 | 160** | 4.8 | 16.8** | 164 |
| 470 | 165** | 9.2 | 19.9** | 1468** |
| 460 | 165** | 6.8 | 11.5 | 142 |
| 437 | 170** | 4.9 | 16.5** | 813** |
| 439 | 170** | 1.2** | 21.3** | 502** |
| 525 | 175** | 11.5 | 15.3 | 1058** |
| 442 | 175** | 4.2 | 17.5** | 328** |
| 456 | 180** | 7.3 | 11.1 | 206 |
| 450 | 180** | 5.0 | 11.8 | 196 |
| 477 | 185** | 3.4** | 31.4** | 369** |
| 508 | 190** | 4.1 | 19.5** | 335** |
| 423 | 190** | 2.5** | 19.0** | 329** |
| 462 | 190** | 3.8 | 11.6 | 276** |
| 523 | 190** | 5.6 | 16.8** | 207 |
| 482 | 190** | 2.9** | 25.1** | 179 |
| 459 | 190** | 5.3 | 19.6** | 167 |
| 543 | 195** | 4.3 | 13.5 | 470** |
| 520 | 195** | 1.7** | 22.2** | 309** |
| 431 | 195** | 7.2 | 13.5 | 251 |
| 513 | 200 | 5.0 | 25.0** | 1184** |
| 534 | 200 | 4.9 | 32.6** | 1080** |
| 515 | 200 | 4.9 | 17.3** | 478** |
| 531 | 200 | 5.1 | 26.8** | 466** |
| 516 | 200 | 3.6** | 17.8** | 279** |
| 526 | 200 | 1.6** | 23.5** | 171 |
| 471 | 205 | 5.7 | 22.0** | 542** |
| 413 | 205 | 2.6** | 20.4** | 304** |
| 497 | 205 | 3.3** | 19.4** | 258 |
| 539 | 205 | 4.1 | 15.4 | 247 |
| 544 | 205 | 12.5 | 11.7 | 233 |
| 540 | 205 | 4.0 | 17.1** | 185 |
| 517 | 205 | 2.2** | 15.0 | 151 |
| 496 | 210 | 3.7** | 15.2 | 1103** |
| 488 | 210 | 16.5 | 21.8** | 600** |
| 416 | 215 | 12.5 | 10.0 | 197 |
| 434 | 220 | 7.1 | 24.8** | 439** |
| 545 | 220 | 11.5 | 14.4 | 407** |
| 547 | 220 | 5.3 | 17.5** | 396** |
| 408 | 220 | 3.2** | 16.4** | 357** |
| 449 | 220 | 3.7** | 13.7 | 272** |
| 507 | 220 | 8.5 | 10.0 | 179 |
| 458 | 225 | 10.5 | 21.1** | 964** |
| 491 | 225 | 7.2 | 16.0 | 472** |
| 529 | 230 | 2.0** | 61.1** | 1172** |
| 415 | 230 | 3.2** | 28.9** | 377** |
| 453 | 230 | 3.6** | 19.8** | 336** |
| 448 | 230 | 5.2 | 13.1 | 319** |
| 498 | 230 | 5.9 | 20.1** | 255 |
| 533 | 230 | 5.7 | 11.7 | 151 |
| 466 | 235 | 35.0 | 12.1 | 617** |
| 537 | 235 | 5.7 | 10.7 | 394** |
| 483 | 235 | 8.6 | 16.6** | 344** |
| 512 | 235 | 3.9 | 12.5 | 190 |
| 452 | 240 | 4.7 | 26.5** | 1068** |
| 454 | 240 | 5.2 | 11.9 | 201 |
| 535 | 240 | 4.4 | 15.3 | 195 |
| 421 | 245 | 10.5 | 12.5 | 464** |
| 469 | 245 | 6.2 | 20.0** | 448** |
| 474 | 245 | 7.3 | 10.3 | 327** |
| 486 | 245 | 9.2 | 12.6 | 156 |
| 536 | 250 | 22.5 | 20.3** | 1068** |
| 475 | 250 | 5.6 | 23.0** | 456** |
| 511 | 250 | 2.7** | 23.1** | 398** |
| 465 | 250 | 4.1 | 23.1** | 323** |
| 506 | 250 | 5.2 | 11.5 | 252 |
| 417 | 250 | 5.5 | 25.2** | 241 |
| 524 | 250 | 2.5** | 14.4 | 212 |
| 411 | 250 | 9.9 | 11.5 | 200 |
| 492 | 250 | 5.2 | 10.7 | 182 |
| 548 | 250 | 2.9** | 12.4 | 179 |
| 441 | 250 | 4.5 | 8.5 | 147 |
| 480 | 255 | 4.8 | 16.9** | 558** |
| 532 | 255 | 7.0 | 14.8 | 419** |
| 464 | 255 | 11.5 | 12.9 | 400** |
| 494 | 255 | 6.2 | 12.1 | 293** |
| 106 | 255 | 4.5 | 11.7 | 203 |
| 546 | 260 | 5.5 | 14.7 | 662** |
| 541 | 260 | 5.4 | 30.8** | 426** |
| 420 | 260 | 5.3 | 13.6 | 347** |
| 500 | 260 | 6.7 | 14.0 | 330** |
| 538 | 260 | 9.3 | 17.3** | 298** |
| 457 | 260 | 2.9** | 12.6 | 286** |
| 472 | 260 | 8.3 | 13.8 | 278** |
| 424 | 260 | 8.3 | 10.1 | 242 |
| 433 | 260 | 6.8 | 10.5 | 197 |
| 425 | 265 | 7.3 | 14.7 | 724** |
| 468 | 265 | 3.8 | 16.7** | 289** |
| 435 | 265 | 7.4 | 14.0 | 150 |
| 499 | 265 | 2.2** | 12.4 | 131 |
| 432 | 270 | 4.3 | 28.3** | 432** |
| 521 | 270 | 3.7** | 15.3 | 349** |
| 549 | 270 | 4.1 | 12.4 | 343** |
| 518 | 270 | 10.0 | 10.1 | 276** |
| 418 | 270 | 26.0 | 9.4 | 213 |
| 419 | 270 | 6.5 | 12.5 | 212 |
| 428 | 270 | 4.2 | 18.7** | 189 |
| 443 | 270 | 8.8 | 12.0 | 187 |
| 446 | 270 | 11.0 | 8.1 | 157 |
| 461 | 275 | 7.6 | 15.1 | 663** |
| 440 | 275 | 4.9 | 12.9 | 248 |
| 436 | 275 | 6.3 | 30.1** | 233 |
| 530 | 275 | 7.4 | 13.6 | 231 |
| 438 | 275 | 4.6 | 8.5 | 221 |
| 527 | 275 | 7.5 | 10.5 | 219 |
| 444 | 275 | 4.0 | 12.2 | 180 |
| 429 | 280 | 5.3 | 15.3 | 463** |
| 503 | 280 | 4.4 | 25.7** | 421** |
| 485 | 280 | 3.5** | 15.6 | 381** |
| 410 | 280 | 14.5 | 10.0 | 201 |
| 487 | 280 | 3.9 | 10.5 | 166 |
| 430 | 280 | 9.2 | 8.8 | 161 |
| 519 | 285 | 3.9 | 22.2** | 919** |
| 476 | 285 | 10.5 | 12.8 | 339** |
| 509 | 285 | 5.4 | 13.0 | 331** |
| 501 | 285 | 5.5 | 12.4 | 252 |
| 542 | 285 | 6.9 | 15.5 | 242 |
| 445 | 285 | 7.2 | 14.9 | 237 |
| 427 | 285 | 4.0 | 17.1** | 233 |
| 490 | 290 | 4.7 | 13.9 | 230 |
| 451 | 290 | 2.1** | 20.0** | 226 |

TABLE 4-continued

SERUM METABOLITE AND VITAMIN LEVELS IN A GERIATRIC POPULATION.

| Patient | $B_{12}$ | Folate | Homocysteine | MMA |
|---|---|---|---|---|
| 414 | 290 | 7.0 | 9.7 | 117 |
| 467 | 290 | 4.1 | 6.5 | 68 |
| 463 | 295 | 5.8 | 12.3 | 296** |
| 473 | 295 | 7.5 | 14.4 | 290** |
| 505 | 295 | 4.1 | 12.4 | 257 |
| 198 | 300 | 11.5 | 10.9 | 323** |
| 195 | 300 | 9.8 | 12.2 | 216 |
| 207 | 305 | 7.7 | 13.2 | 330** |
| 67 | 305 | 8.6 | 15.4 | 312** |
| 50 | 305 | 9.0 | 11.6 | 235 |
| 70 | 305 | 12.5 | 12.7 | 228 |
| 113 | 305 | 5.6 | 13.5 | 201 |
| 39 | 305 | 6.9 | 19.7** | 170 |
| 3 | 305 | 4.2 | 11.5 | 135 |
| 325 | 305 | 14.5 | 9.4 | 94 |
| 368 | 310 | 4.7 | 15.9 | 371** |
| 322 | 310 | 7.8 | 15.3 | 362** |
| 295 | 310 | 7.2 | 13.8 | 305** |
| 347 | 310 | 5.8 | 16.5** | 266 |
| 313 | 310 | 6.1 | 16.5** | 219 |
| 355 | 310 | 5.5 | 15.4 | 138 |
| 291 | 310 | 4.5 | 15.2 | 125 |
| 478 | 315 | 23.0 | 17.7** | 857** |
| 53 | 315 | 5.8 | 12.1 | 505** |
| 240 | 315 | 6.7 | 12.3 | 394** |
| 14 | 315 | 9.6 | 14.2 | 331** |
| 137 | 315 | 7.8 | 24.3** | 306** |
| 254 | 315 | 8.7 | 17.0** | 285** |
| 109 | 315 | 3.7** | 16.5** | 263 |
| 252 | 315 | 5.2 | 10.1 | 241 |
| 186 | 315 | 4.1 | 15.4 | 238 |
| 183 | 315 | 5.5 | 10.7 | 195 |
| 390 | 315 | 6.9 | 10.0 | 188 |
| 267 | 315 | 2.2** | 12.0 | 124 |
| 310 | 320 | 12.0 | 13.8 | 395** |
| 31 | 320 | 17.0 | 12.9 | 334** |
| 88 | 320 | 4.8 | 13.8 | 217 |
| 403 | 320 | 9.6 | 11.3 | 162 |
| 60 | 320 | 6.2 | 11.4 | 155 |
| 315 | 320 | 6.4 | 9.9 | 136 |
| 175 | 325 | 6.3 | 17.8** | 486** |
| 317 | 325 | 22.0 | 14.0 | 294** |
| 18 | 325 | 6.3 | 11.1 | 241 |
| 247 | 325 | 13.5 | 13.2 | 231 |
| 223 | 325 | 9.2 | 12.6 | 203 |
| 132 | 325 | 3.7** | 15.4 | 184 |
| 168 | 325 | 4.3 | 10.2 | 174 |
| 238 | 325 | 5.5 | 9.9 | 166 |
| 117 | 325 | 5.2 | 15.0 | 154 |
| 404 | 330 | 2.5** | 33.1** | 1085** |
| 138 | 330 | 4.8 | 11.3 | 360** |
| 316 | 330 | 3.6** | 10.2 | 272** |
| 61 | 330 | 5.1 | 12.5 | 242 |
| 333 | 330 | 34.0 | 9.2 | 235 |
| 16 | 330 | 4.6 | 13.3 | 211 |
| 276 | 330 | 5.7 | 11.9 | 200 |
| 391 | 330 | 4.1 | 8.4 | 184 |
| 362 | 330 | 9.2 | 11.7 | 178 |
| 1 | 330 | 9.9 | 8.9 | 170 |
| 379 | 335 | 16.0 | 12.1 | 471** |
| 147 | 335 | 9.0 | 9.7 | 427** |
| 89 | 335 | 8.0 | 15.3 | 385** |
| 211 | 335 | 5.0 | 12.2 | 374** |
| 45 | 335 | 5.9 | 16.3** | 250 |
| 47 | 335 | 5.0 | 13.6 | 249 |
| 402 | 335 | 4.7 | 13.5 | 230 |
| 314 | 335 | 7.6 | 9.7 | 203 |
| 150 | 335 | 4.8 | 11.2 | 119 |
| 120 | 340 | 1.9** | 21.0** | 775** |
| 284 | 340 | 7.2 | 25.6** | 439** |
| 230 | 340 | 14.0 | 11.4 | 419** |
| 149 | 340 | 8.8 | 18.9** | 337** |
| 269 | 340 | 3.9 | 16.2 | 302** |
| 197 | 340 | 10.5 | 12.8 | 233 |
| 19 | 340 | 9.6 | 11.0 | 232 |
| 422 | 340 | 3.1** | 14.4 | 188 |
| 196 | 340 | 11.5 | 8.9 | 169 |
| 40 | 345 | 8.7 | 14.6 | 610** |
| 244 | 345 | 8.6 | 15.8 | 461** |
| 287 | 345 | 5.7 | 18.1** | 427** |
| 100 | 345 | 8.3 | 14.8 | 403** |
| 383 | 345 | 4.3 | 27.2** | 284** |
| 62 | 345 | 19.5 | 9.6 | 250 |
| 350 | 345 | 8.0 | 10.0 | 249 |
| 65 | 345 | 8.0 | 10.2 | 247 |
| 307 | 345 | 16.5 | 11.6 | 208 |
| 69 | 345 | 17.0 | 9.9 | 197 |
| 328 | 345 | 7.5 | 8.9 | 192 |
| 43 | 345 | 6.0 | 13.2 | 191 |
| 222 | 345 | 6.1 | 9.2 | 175 |
| 306 | 345 | 4.3 | 17.2** | 160 |
| 154 | 345 | 7.1 | 10.2 | 148 |
| 94 | 350 | 4.8 | 16.1 | 302** |
| 201 | 350 | 6.1 | 9.9 | 200 |
| 13 | 350 | 5.1 | 10.9 | 193 |
| 236 | 355 | 7.2 | 14.8 | 309** |
| 191 | 355 | 5.8 | 15.3 | 257 |
| 481 | 355 | 5.2 | 17.1** | 134 |
| 92 | 360 | 4.2 | 25.2** | 321** |
| 324 | 360 | 3.8 | 16.6** | 264 |
| 87 | 360 | 3.3** | 13.3 | 200 |
| 46 | 360 | 5.4 | 11.1 | 179 |
| 289 | 360 | 9.5 | 7.9 | 129 |
| 392 | 360 | 5.1 | 10.3 | 125 |
| 320 | 365 | 6.4 | 17.3** | 240 |
| 134 | 365 | 13.5 | 11.8 | 238 |
| 239 | 365 | 7.7 | 13.2 | 236 |
| 326 | 365 | 6.0 | 10.9 | 180 |
| 364 | 365 | 4.1 | 13.9 | 154 |
| 218 | 365 | 7.5 | 11.2 | 126 |
| 216 | 365 | 6.2 | 12.2 | 119 |
| 248 | 365 | 5.7 | 13.3 | 117 |
| 375 | 370 | 4.1 | 20.7** | 532** |
| 288 | 370 | 6.4 | 18.8** | 436** |
| 161 | 370 | 6.3 | 11.2 | 340** |
| 224 | 370 | 19.5 | 9.8 | 286** |
| 330 | 370 | 18.0 | 12.2 | 228 |
| 334 | 370 | 12.5 | 8.7 | 172 |
| 275 | 370 | 6.9 | 12.7 | 162 |
| 54 | 375 | 7.3 | 10.1 | 583** |
| 185 | 375 | 9.3 | 10.5 | 386** |
| 52 | 375 | 8.1 | 15.5 | 291** |
| 366 | 375 | 5.0 | 12.5 | 280** |
| 93 | 375 | 3.3** | 16.2 | 248 |
| 151 | 375 | 2.9** | 12.3 | 235 |
| 85 | 375 | 6.7 | 14.8 | 217 |
| 294 | 375 | 7.0 | 12.2 | 184 |
| 361 | 375 | 7.9 | 10.7 | 179 |
| 318 | 375 | 5.5 | 13.7 | 160 |
| 386 | 375 | 7.6 | 10.4 | 153 |
| 304 | 375 | 9.1 | 9.4 | 132 |
| 228 | 380 | 7.7 | 17.1** | 320** |
| 110 | 380 | 4.0 | 7.2 | 135 |
| 204 | 380 | 5.7 | 10.6 | 91 |
| 348 | 385 | 2.3** | 17.4** | 368** |
| 146 | 385 | 11.5 | 12.5 | 253 |
| 260 | 385 | 5.5 | 13.7 | 211 |
| 136 | 385 | 3.6** | 19.8** | 205 |
| 338 | 385 | 5.0 | 16.2 | 180 |
| 376 | 385 | 3.6** | 13.7 | 154 |
| 194 | 385 | 12.5 | 7.9 | 153 |
| 504 | 385 | 38.0 | 9.5 | 138 |
| 160 | 390 | 8.1 | 24.7** | 475** |
| 354 | 390 | 11.5 | 12.8 | 212 |
| 25 | 390 | 5.1 | 11.3 | 205 |
| 387 | 390 | 8.7 | 8.4 | 162 |
| 86 | 390 | 21.0 | 12.6 | 133 |
| 133 | 390 | 3.9 | 11.3 | 113 |

TABLE 4-continued

SERUM METABOLITE AND VITAMIN LEVELS IN A GERIATRIC POPULATION.

| Patient | B$_{12}$ | Folate | Homocysteine | MMA |
|---|---|---|---|---|
| 331 | 395 | 12.0 | 20.1** | 638** |
| 130 | 395 | 10.5 | 10.8 | 256 |
| 82 | 395 | 2.8** | 9.8 | 236 |
| 119 | 395 | 12.5 | 16.3** | 209 |
| 380 | 395 | 10.5 | 14.3 | 159 |
| 373 | 395 | 5.5 | 11.6 | 152 |
| 256 | 395 | 10.5 | 9.9 | 149 |
| 384 | 395 | 7.3 | 14.7 | 116 |
| 105 | 400 | 19.0 | 10.5 | 322** |
| 251 | 400 | 4.8 | 14.9 | 289** |
| 352 | 400 | 11.5 | 9.6 | 181 |
| 279 | 400 | 4.5 | 11.7 | 170 |
| 339 | 400 | 7.4 | 13.6 | 168 |
| 381 | 405 | 6.7 | 12.4 | 294** |
| 285 | 405 | 7.0 | 14.2 | 281** |
| 340 | 405 | 3.6** | 19.6** | 275** |
| 51 | 405 | 6.5 | 14.3 | 233 |
| 33 | 405 | 6.5 | 9.6 | 207 |
| 268 | 405 | 3.3** | 14.9 | 205 |
| 73 | 405 | 5.2 | 13.1 | 172 |
| 17 | 410 | 7.5 | 16.2 | 473** |
| 286 | 410 | 4.7 | 18.8** | 415** |
| 140 | 410 | 5.9 | 21.7** | 302** |
| 116 | 410 | 6.8 | 14.5 | 218 |
| 396 | 410 | 5.6 | 16.1 | 190 |
| 356 | 410 | 1.9** | 27.6** | 149 |
| 237 | 410 | 3.6** | 16.6** | 122 |
| 112 | 410 | 5.5 | 8.9 | 107 |
| 259 | 410 | 4.7 | 11.6 | 99 |
| 176 | 415 | 5.2 | 21.9** | 453** |
| 193 | 415 | 10.5 | 11.3 | 163 |
| 323 | 415 | 6.1 | 9.6 | 163 |
| 202 | 415 | 11.5 | 9.4 | 150 |
| 398 | 415 | 8.0 | 12.6 | 134 |
| 321 | 420 | 5.2 | 10.7 | 383** |
| 142 | 420 | 29.0 | 8.3 | 234 |
| 327 | 420 | 3.2** | 14.6 | 203 |
| 342 | 420 | 7.3 | 9.4 | 156 |
| 170 | 420 | 20.5 | 10.3 | 142 |
| 345 | 420 | 29.5 | 13.2 | 136 |
| 302 | 420 | 8.6 | 8.8 | 128 |
| 115 | 425 | 6.3 | 22.2** | 628** |
| 97 | 425 | 12.5 | 19.8** | 313** |
| 246 | 425 | 8.7 | 15.1 | 241 |
| 72 | 425 | 10.5 | 13.5 | 241 |
| 365 | 425 | 6.7 | 16.7** | 237 |
| 139 | 425 | 12.5 | 10.4 | 224 |
| 143 | 425 | 8.1 | 13.5 | 216 |
| 426 | 425 | 19.5 | 14.5 | 201 |
| 303 | 425 | 3.0** | 14.5 | 154 |
| 388 | 425 | 6.2 | 12.3 | 135 |
| 127 | 425 | 6.7 | 8.4 | 100 |
| 262 | 430 | 10.0 | 12.1 | 323** |
| 270 | 430 | 4.8 | 12.9 | 293** |
| 514 | 430 | 4.3 | 12.9 | 197 |
| 341 | 430 | 3.5** | 19.9** | 190 |
| 278 | 430 | 5.2 | 10.8 | 182 |
| 370 | 430 | 11.0 | 15.3 | 174 |
| 55 | 430 | 7.6 | 11.0 | 162 |
| 274 | 430 | 5.0 | 8.2 | 131 |
| 367 | 430 | 17.5 | 8.0 | 126 |
| 98 | 430 | 13.5 | 12.8 | 125 |
| 337 | 435 | 13.5 | 14.1 | 395** |
| 309 | 435 | 8.7 | 12.9 | 349** |
| 305 | 435 | 17.5 | 15.4 | 187 |
| 144 | 435 | 25.0 | 8.9 | 167 |
| 34 | 435 | 8.6 | 7.6 | 157 |
| 234 | 435 | 9.7 | 9.2 | 116 |
| 123 | 440 | 9.6 | 12.2 | 622** |
| 200 | 440 | 4.8 | 12.4 | 257 |
| 250 | 440 | 7.5 | 12.9 | 248 |
| 107 | 440 | 6.3 | 14.7 | 183 |
| 300 | 440 | 6.5 | 7.9 | 123 |
| 374 | 445 | 5.4 | 14.0 | 247 |
| 372 | 445 | 11.0 | 11.0 | 181 |
| 36 | 445 | 4.0 | 10.0 | 181 |
| 271 | 445 | 7.2 | 10.4 | 124 |
| 242 | 445 | 15.5 | 9.6 | 112 |
| 264 | 445 | 6.0 | 10.7 | 100 |
| 172 | 450 | 11.5 | 14.9 | 607** |
| 32 | 450 | 11.5 | 13.6 | 362** |
| 346 | 450 | 13.5 | 15.8 | 330** |
| 41 | 450 | 8.5 | 11.4 | 194 |
| 95 | 450 | 5.1 | 12.5 | 182 |
| 357 | 455 | 6.3 | 14.4 | 296** |
| 319 | 455 | 17.0 | 10.2 | 147 |
| 308 | 455 | 15.0 | 9.8 | 131 |
| 235 | 455 | 23.0 | 9.0 | 114 |
| 349 | 455 | 9.2 | 8.3 | 82 |
| 178 | 460 | 5.6 | 20.6** | 473** |
| 312 | 460 | 4.7 | 14.4 | 197 |
| 79 | 460 | 5.0 | 10.4 | 173 |
| 131 | 460 | 18.0 | 10.2 | 162 |
| 243 | 460 | 2.6** | 11.6 | 160 |
| 261 | 465 | 7.7 | 10.6 | 252 |
| 378 | 465 | 5.4 | 13.2 | 221 |
| 49 | 465 | 47.0 | 10.8 | 179 |
| 226 | 465 | 7.7 | 10.2 | 173 |
| 377 | 465 | 5.6 | 8.5 | 143 |
| 253 | 465 | 10.0 | 7.0 | 138 |
| 76 | 470 | 12.5 | 14.8 | 304** |
| 203 | 470 | 15.0 | 7.6 | 233 |
| 296 | 470 | 23.5 | 11.0 | 161 |
| 382 | 470 | 5.3 | 11.1 | 109 |
| 6 | 475 | 10.5 | 12.5 | 232 |
| 75 | 475 | 4.5 | 8.1 | 150 |
| 332 | 475 | 9.4 | 10.0 | 144 |
| 290 | 475 | 14.0 | 9.1 | 143 |
| 128 | 475 | 5.9 | 9.3 | 133 |
| 124 | 475 | 6.0 | 13.5 | 111 |
| 177 | 475 | 8.8 | 9.1 | 106 |
| 126 | 480 | 11.0 | 11.0 | 212 |
| 283 | 480 | 5.2 | 10.6 | 175 |
| 209 | 480 | 10.5 | 10.5 | 175 |
| 293 | 480 | 6.8 | 15.5 | 135 |
| 121 | 485 | 4.7 | 20.0** | 345** |
| 282 | 485 | 12.0 | 10.9 | 236 |
| 71 | 485 | 13.5 | 8.1 | 168 |
| 385 | 485 | 9.0 | 14.1 | 128 |
| 190 | 495 | 9.9 | 10.4 | 410** |
| 210 | 495 | 8.6 | 12.0 | 243 |
| 155 | 495 | 5.9 | 10.4 | 219 |
| 336 | 495 | 13.5 | 9.9 | 135 |
| 280 | 500 | 8.7 | 14.5 | 334** |
| 96 | 500 | 4.7 | 10.8 | 237 |
| 145 | 500 | 5.9 | 17.5** | 233 |
| 199 | 500 | 4.2 | 13.8 | 199 |
| 489 | 500 | 11.5 | 9.7 | 198 |
| 217 | 500 | 6.4 | 9.6 | 166 |
| 90 | 500 | 7.5 | 8.5 | 106 |
| 164 | 510 | 5.2 | 23.8** | 408** |
| 343 | 510 | 4.5 | 13.7 | 284** |
| 42 | 510 | 4.9 | 7.4 | 233 |
| 351 | 510 | 8.5 | 11.0 | 207 |
| 299 | 510 | 12.0 | 8.0 | 104 |
| 99 | 520 | 10.5 | 25.8** | 322** |
| 114 | 520 | 30.0 | 10.9 | 220 |
| 369 | 520 | 29.0 | 16.7** | 206 |
| 37 | 520 | 10.5 | 8.6 | 191 |
| 215 | 520 | 6.7 | 16.8** | 151 |
| 401 | 520 | 7.5 | 12.6 | 148 |
| 229 | 520 | 7.9 | 11.0 | 116 |
| 135 | 520 | 3.2** | 8.3 | 88 |
| 81 | 530 | 6.8 | 14.8 | 372** |
| 91 | 530 | 14.5 | 10.6 | 228 |
| 167 | 530 | 23.5 | 9.2 | 176 |
| 181 | 530 | 5.5 | 9.3 | 171 |
| 56 | 530 | 20.0 | 8.3 | 163 |

TABLE 4-continued

SERUM METABOLITE AND VITAMIN LEVELS IN A GERIATRIC POPULATION.

| Patient | $B_{12}$ | Folate | Homocysteine | MMA |
|---|---|---|---|---|
| 5 | 530 | 13.5 | 8.1 | 159 |
| 180 | 540 | 12.0 | 9.0 | 216 |
| 311 | 540 | 4.1 | 13.3 | 214 |
| 389 | 540 | 3.9 | 13.9 | 169 |
| 125 | 540 | 5.5 | 13.0 | 159 |
| 35 | 540 | 22.5 | 11.0 | 123 |
| 104 | 550 | 10.5 | 16.5** | 544** |
| 393 | 550 | 4.9 | 11.9 | 339** |
| 394 | 550 | 23.0 | 14.0 | 278** |
| 292 | 550 | 6.9 | 16.2 | 263 |
| 163 | 550 | 6.7 | 14.3 | 219 |
| 66 | 550 | 10.5 | 11.6 | 206 |
| 29 | 550 | 17.5 | 9.6 | 191 |
| 227 | 550 | 7.9 | 11.7 | 154 |
| 38 | 550 | 7.5 | 11.9 | 152 |
| 241 | 550 | 10.5 | 9.8 | 100 |
| 102 | 550 | 9.7 | 8.6 | 91 |
| 77 | 560 | 24.0 | 14.8 | 554** |
| 162 | 560 | 10.5 | 11.8 | 275** |
| 273 | 560 | 8.7 | 9.4 | 180 |
| 80 | 560 | 6.3 | 11.2 | 108 |
| 255 | 560 | 8.8 | 9.9 | 93 |
| 122 | 570 | 66.0 | 13.8 | 304** |
| 208 | 570 | 34.0 | 10.2 | 255 |
| 23 | 570 | 21.5 | 8.3 | 241 |
| 447 | 570 | 25.0 | 10.0 | 164 |
| 225 | 570 | 5.7 | 12.2 | 154 |
| 174 | 570 | 7.1 | 11.0 | 127 |
| 11 | 570 | 19.0 | 8.9 | 113 |
| 165 | 580 | 10.5 | 14.8 | 226 |
| 182 | 580 | 8.9 | 8.2 | 189 |
| 245 | 590 | 15.5 | 10.0 | 262 |
| 83 | 590 | 17.5 | 8.3 | 199 |
| 166 | 590 | 11.5 | 9.4 | 188 |
| 158 | 590 | 7.3 | 10.7 | 166 |
| 187 | 590 | 4.5 | 11.0 | 146 |
| 156 | 590 | 23.5 | 11.3 | 112 |
| 231 | 600 | 9.5 | 9.0 | 192 |
| 78 | 600 | 11.5 | 9.4 | 151 |
| 329 | 610 | 15.0 | 7.3 | 312** |
| 57 | 610 | 16.0 | 11.9 | 286** |
| 7 | 610 | 12.0 | 10.4 | 195 |
| 277 | 610 | 9.5 | 7.8 | 153 |
| 108 | 620 | 13.5 | 8.4 | 191 |
| 205 | 620 | 18.0 | 7.5 | 145 |
| 263 | 620 | 9.8 | 10.2 | 101 |
| 9 | 630 | 4.9 | 11.4 | 300** |
| 111 | 630 | 8.3 | 11.1 | 276** |
| 68 | 630 | 11.5 | 8.9 | 143 |
| 399 | 630 | 14.0 | 11.0 | 90 |
| 266 | 640 | 5.1 | 15.7 | 364** |
| 12 | 640 | 24.5 | 9.0 | 233 |
| 152 | 640 | 8.1 | 10.0 | 209 |
| 405 | 640 | 7.0 | 12.8 | 186 |
| 27 | 640 | 22.5 | 8.4 | 136 |
| 258 | 640 | 8.3 | 11.2 | 120 |
| 249 | 640 | 8.7 | 9.1 | 81 |
| 297 | 650 | 16.0 | 10.0 | 279** |
| 192 | 650 | 4.9 | 14.9 | 213 |
| 257 | 650 | 3.3** | 16.3** | 208 |
| 184 | 650 | 12.5 | 9.9 | 193 |
| 58 | 650 | 18.5 | 10.7 | 172 |
| 301 | 650 | 16.0 | 15.5 | 162 |
| 397 | 650 | 12.5 | 8.4 | 146 |
| 272 | 650 | 11.0 | 7.4 | 120 |
| 153 | 650 | 7.1 | 13.1 | 116 |
| 406 | 650 | 6.6 | 5.8 | 81 |
| 10 | 660 | 9.0 | 7.6 | 154 |
| 26 | 660 | 22.0 | 8.3 | 132 |
| 265 | 670 | 3.9 | 19.3** | 509** |
| 359 | 670 | 21.0 | 8.3 | 269 |
| 48 | 670 | 32.0 | 9.9 | 262 |
| 335 | 670 | 11.5 | 8.1 | 121 |
| 189 | 680 | 6.6 | 17.9** | 358** |
| 220 | 680 | 15.5 | 10.9 | 115 |
| 15 | 690 | 13.5 | 13.4 | 159 |
| 44 | 700 | 20.0 | 12.7 | 244 |
| 21 | 700 | 13.5 | 10.2 | 129 |
| 74 | 700 | 15.0 | 7.1 | 65 |
| 4 | 710 | 29.0 | 8.5 | 266 |
| 353 | 710 | 11.5 | 11.4 | 206 |
| 281 | 710 | 10.5 | 9.6 | 185 |
| 2 | 710 | 8.0 | 8.5 | 109 |
| 212 | 740 | 20.0 | 11.1 | 250 |
| 8 | 740 | 12.0 | 11.5 | 216 |
| 206 | 750 | 12.5 | 8.3 | 116 |
| 101 | 770 | 14.5 | 12.7 | 372** |
| 344 | 770 | 32.0 | 11.7 | 297** |
| 20 | 770 | 35.0 | 10.1 | 245 |
| 407 | 770 | 10.5 | 12.0 | 110 |
| 360 | 780 | 2.7** | 20.9** | 157 |
| 232 | 790 | 15.5 | 10.1 | 151 |
| 141 | 790 | 12.5 | 9.5 | 74 |
| 129 | 800 | 8.7 | 11.7 | 211 |
| 188 | 800 | 15.0 | 12.3 | 174 |
| 400 | 800 | 12.5 | 10.3 | 156 |
| 24 | 810 | 23.0 | 7.5 | 194 |
| 173 | 830 | 35.0 | 11.4 | 243 |
| 214 | 830 | 21.5 | 12.0 | 187 |
| 63 | 830 | 13.8 | 8.8 | 185 |
| 148 | 830 | 45.0 | 7.1 | 146 |
| 84 | 830 | 23.5 | 7.0 | 136 |
| 179 | 830 | 16.5 | 6.6 | 96 |
| 171 | 840 | 23.5 | 11.2 | 195 |
| 28 | 870 | 5.8 | 15.9 | 197 |
| 233 | 870 | 7.9 | 12.7 | 169 |
| 221 | 870 | 40.0 | 7.0 | 126 |
| 371 | 880 | 20.0 | 8.5 | 152 |
| 213 | 890 | 10.5 | 18.0** | 231 |
| 358 | 900 | 21.0 | 8.3 | 149 |
| 298 | 910 | 15.5 | 10.2 | 221 |
| 118 | 910 | 100.0 | 9.7 | 170 |
| 479 | 950 | 11.5 | 12.1 | 188 |
| 30 | 950 | 6.2 | 10.5 | 170 |
| 159 | 1000 | 9.5 | 8.7 | 281** |
| 219 | 1050 | 37.0 | 14.3 | 313** |
| 103 | 1050 | 12.5 | 10.3 | 154 |
| 59 | 1150 | 17.5 | 7.3 | 180 |
| 157 | 1250 | 12.0 | 14.0 | 206 |
| 363 | 1350 | 28.0 | 10.4 | 190 |
| 22 | 1400 | 13.5 | 10.4 | 233 |
| 64 | 1400 | 31.0 | 9.7 | 149 |
| 169 | 1450 | 15.0 | 9.5 | 150 |

I claim:

1. A method of treating or preventing elevated serum metabolite levels of at least one of homocysteine, methylmalonic acid, cystathionine, or 2-methylcitric acid comprising periodically administering orally a single formulation having between 0.3–10 mg vitamin $B_{12}$ and 0.1–0.4 mg folic acid.

2. The method of claim 1 wherein the formulation includes approximately 2 mg vitamin $B_{12}$ and 0.4 mg folic acid.

3. The method of claim 1 wherein said metabolite is homocysteine.

4. The method of claim 1 wherein said metabolite is methylmalonic acid.

5. The method of claim 1 wherein said metabolite is cystathionine.

6. The method of claim 1 wherein said metabolite is 2-methylcitric acid.

7. A method of treating or preventing elevated serum metabolite levels of at least one of homocysteine, methylmalonic acid, cystathionine, or 2-methylcitric acid comprising periodically administering orally a single formulation having between 0.3–10 mg vitamin $B_{12}$, 0.1–0.4 mg folic acid, and 5–75 mg $B_6$.

8. The method of claim 7 wherein the formulation includes approximately 2 mg vitamin $B_{12}$ and 0.4 mg folic acid and 25 mg $B_6$.

9. The method of claim 7 wherein said metabolite is homocysteine.

10. The method of claim 7 wherein said metabolite is methylmalonic acid.

11. The method of claim 7 wherein said metabolite is cystathionine.

12. The method of claim 7 wherein said metabolite is 2-methylcitric acid.

13. A method of treating or preventing elevated serum metabolic levels of at least one of homocysteine, methylmalonic acid, cystathionine, or 2-methylcitric acid comprising periodically administering orally a single formulation having between 0.3–10 mg vitamin $B_{12}$ and 0.4–10.0 mg folic acid.

14. The method of claim 13 wherein the formulation includes approximately 2 mg vitamin $B_{12}$ and 1.0 mg folic acid.

15. The method of claim 13 wherein said metabolite is homocysteine.

16. The method of claim 13 wherein said metabolite is methylmalonic acid.

17. The method of claim 13 wherein said metabolite is cystathionine.

18. The method of claim 13 wherein said metabolite is 2-methylcitric acid.

19. A method of treating or preventing elevated serum metabolite levels of at least one of homocysteine, methylmalonic acid, cystathionine, or 2-methylcitric acid comprising periodically administering orally a single formulation having between 0.3–10 mg vitamin $B_{12}$, 0.4–10 mg folic acid, and 5–75 mg $B_6$.

20. The method of claim 19 wherein the formulation includes approximately 2 mg vitamin $B_{12}$ and 1.0 mg folic acid and 25 mg $B_{12}$.

21. The method of claim 19 wherein said metabolite is homocysteine.

22. The method of claim 19 wherein said metabolite is methylmalonic acid.

23. The method of claim 19 wherein said metabolite is cystathionine.

24. The method of claim 19 wherein said metabolite is 2-methylcitric acid.

25. A method of lowering serum metabolite levels of at least one of homocysteine, methylmalonic acid, cystathionine, or 2-methylcitric acid comprising periodically administering orally a single formulation having between 0.3–10 mg vitamin $B_{12}$, 0.1–0.4 mg folic acid.

26. A method of claim 25 wherein the formulation includes approximately 2 mg vitamin $B_{12}$ and 0.4 mg folic acid.

27. The method of claim 25 wherein said metabolite is homocysteine.

28. The method of claim 25 wherein said metabolite is methylmalonic acid.

29. The method of claim 25 wherein said metabolite is cystathionine.

30. The method of claim 25 wherein said metabolite is 2-methylcitric acid.

31. A method of lowering serum metabolite levels of at least one of homocysteine, methylmalonic acid, cystathionine, or 2-methylcitric acid comprising periodically administering orally a single formulation having between 0.3–10 mg vitamin $B_{12}$, 0.1–0.4 mg folic acid, and 5–75 mg $B_6$.

32. The method of claim 31 wherein the formulation includes approximately 2 mg vitamin $B_{12}$ and 0.4 mg folic acid and 25 mg $B_6$.

33. The method of claim 31 wherein said metabolite is homocysteine.

34. The method of claim 31 wherein said metabolite is methylmalonic acid.

35. The method of claim 31 wherein said metabolite is cystathionine.

36. The method of claim 31 wherein said metabolite is 2-methylcitric acid.

37. A method of lowering serum metabolite levels of at least one of homocysteine, methylmalonic acid, cystathionine, or 2-methylcitric acid comprising periodically administering orally a single formulation having between 0.3–10 mg vitamin $B_{12}$ and 0.4–10.0 mg folic acid.

38. The method of claim 37 wherein the formulation includes approximately 2 mg vitamin $B_{12}$ and 1.0 mg folic acid.

39. The method of claim 37 wherein said metabolite is homocysteine.

40. The method of claim 37 wherein said metabolite is methylmalonic acid.

41. The method of claim 37 wherein said metabolite is cystathionine.

42. The method of claim 37 wherein said metabolite is 2-methylcitric acid.

43. A method of lowering serum metabolite levels of at least one of homocysteine, methylmalonic acid, cystathionine, or 2-methylcitric acid comprising periodically administering orally a single formulation having between 0.3–10 mg vitamin $B_{12}$, 0.4–10 mg folic acid, and 5–75 mg $B_6$.

44. The method of claim 43 wherein the formulation includes approximately 2 mg vitamin $B_{12}$ and 1.0 mg folic acid and 25 mg $B_6$.

45. The method of claim 43 wherein said metabolite is homocysteine.

46. The method of claim 43 wherein said metabolite is methylmalonic acid.

47. The method of claim 43 wherein said metabolite is cystathionine.

48. The method of claim 43 wherein said metabolite is 2-methylcitric acid.

* * * * *

UNITED STATES PATENT AND TRADEMARK OFFICE
CERTIFICATE OF CORRECTION

PATENT NO : 5,795,873

DATED : Aug. 18, 1998

INVENTOR(S): Robert H. Allen and Sally P. Stabler

It is certified that error appears in the above-identified patent and that said Letters Patent is hereby corrected as shown below:

Cover page, the line listing the inventors should read: Robert H. Allen; Sally P. Stabler, both of Denver, Colorado.

Cover page, first column, line 11 under References Cited, Publications: replace "artherosclerotic" with --atherosclerotic--.

Cover page, second column, the following lines under References Cited, Publications should read as follows: line 11, replace "roboflavin" with --riboflavin--; line 19, between "Academy of Sciences" and "pp. 197-204", insert --1992--; line 29, between "Nutrition Reviews" and "pp. 247-249", insert --1989--.

In line 18 of the Abstract, replace "eliminate" with --eliminates--.

Second cover page, first column, line 6 under Other Publications, replace "Physcicians" with --Physicians--.

Second cover page, second column, the following lines under Other Publications should read as follows: line 4, before "pp. 136-143", insert --1996--; at line 5, replace "Hemocystinuira" with --Homocystinuria--.

Column 2, line 64, replace "confusions" with --convulsions--.

Column 3, line 48, replace "Benvange" with --Benevenga--.

Column 3, line 63, replace "hyperhomocysteinaemia" with --hyperhomocysteinemia--.

Column 5, line 64, replace "invention is" with --invention uses--.

Column 6, line 1, replace "0.1-0.4 folate" with --0.1-0.4 mg folate--.

Column 6, line 9, replace "0.4-1.0 mg" with --0.4-10.0 mg--.

Column 7, line 3, replace "more the" with --more of the--.

UNITED STATES PATENT AND TRADEMARK OFFICE
CERTIFICATE OF CORRECTION

PATENT NO : 5,795,873
DATED : Aug. 18, 1998
INVENTOR(S): Robert H. Allen and Sally P. Stabler It is certified that error appears in the above-identified patent and that said Letters Patent is hereby corrected as shown below:

Column 7, line 7, replace "metabolites" with --metabolite--.
Column 8, line 51, replace "result" with --results--.
Column 9, line 20, replace "creatine" with --creatinine--.
Column 9, line 24, replace "+2" with --$\pm 2$--.
Column 10, line 41, replace "populations" with --population--.

Signed and Sealed this

Twenty-fifth Day of July, 2000

Attest:

Attesting Officer

Q. TODD DICKINSON

Director of Patents and Trademarks